US007776894B2

(12) United States Patent
Ronai et al.

(10) Patent No.: US 7,776,894 B2
(45) Date of Patent: Aug. 17, 2010

(54) COMPOSITIONS AND METHODS FOR INHIBITING GROWTH AND METASTASIS OF MELANOMA

(75) Inventors: Ze'ev A. Ronai, San Diego, CA (US); Anindita Bhoumik, San Diego, CA (US); Nicholas D. P. Cosford, San Diego, CA (US); Russell Dahl, Carlsbad, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 0 days.

(21) Appl. No.: 12/192,753

(22) Filed: Aug. 15, 2008

(65) Prior Publication Data

US 2009/0054438 A1     Feb. 26, 2009

Related U.S. Application Data

(60) Provisional application No. 60/965,178, filed on Aug. 17, 2007.

(51) Int. Cl.
  *A61K 31/40* (2006.01)
  *A61K 31/4406* (2006.01)
  *A61K 31/215* (2006.01)
  *A61K 31/165* (2006.01)
  *A61K 31/16* (2006.01)

(52) U.S. Cl. .................. 514/357; 514/423; 514/510; 514/623

(58) Field of Classification Search .............. None
See application file for complete search history.

(56) References Cited

U.S. PATENT DOCUMENTS

| 7,314,855 | B2 | 1/2008 | Ronai |
| 2005/0261363 | A1 | 11/2005 | Lee et al. |
| 2007/0093456 | A1 | 4/2007 | Cai et al. |
| 2008/0139475 | A1 | 6/2008 | Ronai |

FOREIGN PATENT DOCUMENTS

WO    WO 2007/077203     7/2007

OTHER PUBLICATIONS

Abbas et al. "Preclinical studies of Celastrol and Acetyl Isogambogic Acid in Melanoma," Clin. Cancer Res., 13:6769-6778 (2007).*
Lage et al. British Journal of Cancer (2000) 82 (2), pp. 488-491.*
Nagase et al. Biosci. Biotechnol. Biochem. (2003) 67 (9) pp. 1883-1887.*
Selzer et al. Journal of Investigative Dermatology, vol. 114, No. 5, May 2000.*
Abbas et al., "Preclinical Studies of Celastrol and Acetyl Isogambogic Acid in Melanoma," Clin Cancer Res, 13:6769-6778 (2007).

Berger et al., "Subcellular Localization of Activating Transcription Factor 2 in Melanoma Specimens Predicts Patient Survival," *Cancer Res*, 63:8103-8107 (2003).
Bhoumik et al., "Activating Transcription Factor 2-Derived Peptides Alter Resistance of Human Tumor Cell Lines to Ultraviolet Irradiation and Chemical Treatment," *Clin Cancer Res*, 7:331-342 (2001).
Bhoumik et al., "An ATF2-Derived Peptide Sensitizes Melanomas to Apoptosis and Inhibits their Growth and Metastasis," *J Clin Invest*, 110:643-650 (2002).
Bhoumik et al., "Transcriptional Switch by Activating Transcription Factor 2-Derived Peptide Sensitizes Melanoma Cells to Apoptosis and Inhibits their Tumorigenicity," *PNAS*, 101:4222-4227 (2004).
Bhoumik et al., "Inhibition of Melanoma Growth and Metastasis by ATF2-Derived Peptides," *Cancer Res*, 64:8222-8230 (2004).
Bhoumik et al., "Suppressor Role of Activating Transcription Factor 2 (ATF2) in Skin Cancer," *PNAS*, 105:1674-1679 (2008).
Guo et al., "General Gambogic Acids Inhibited Growth of Human Hepatoma SMMC-7721 Cells in Vitro and in Nude Mice," *Acta Pharmacol Sin*, 25:769-774 (2004).
Pandey et al., "Gambogic Acid, a Novel Ligand for Transferrin Receptor, Potentiates TNF-Induced Apoptosis Through Modulation of the Nuclear Factor-κB Signaling Pathway," *Blood*, 110:3517-3525 (2007).
Selzer et al., "Effects of Betulinic Acid Alone and in Combination with Irradiation in Human Melanoma Cells," *J Invest Dermatol*, 114:935-940 (2000).
Yang et al., "Celastrol, a Triterpene Extracted from the Chinese "Thunder of God Vine," Is a Potent Prosteasome Inhibitor and Suppresses Human Prostate Cancer Growth in Nude Mice," *Cancer Res*, 66:4758-4765 (2006).
Yu et al., "Gambogic Acid-Induced $G_2$/M Phase Cell-Cycle Arrest via Disturbing CDK7-Mediated Phosphorylation of CDC2/p34 in Human Gastric Carcinoma BGC-823 Cells," *Carcinogenesis*, 28:632-638 (2007).
Zhang et al., "Discovery, Characterization and SAR of Gambogic Acid as a Potent Apoptosis Inducer by a HTS Assay," *Bioorg Med Chem*, 12:309-317 (2004).

* cited by examiner

Primary Examiner—Kamal A Saeed
Assistant Examiner—Alicia L Fierro
(74) Attorney, Agent, or Firm—DLA Piper LLP (US)

(57) ABSTRACT

There are provided methods of inhibiting growth and metastasis of melanoma, methods of sensitizing melanoma cells to apoptosis, and methods of treating a subject having melanoma using acetyl isogambogic acid, celastrol, or a derivative thereof. There are further provided derivatives of celastrol and compositions comprising acetyl isogambogic acid, celastrol, or a derivative thereof.

12 Claims, 7 Drawing Sheets

US 7,776,894 B2

COMPOSITIONS AND METHODS FOR INHIBITING GROWTH AND METASTASIS OF MELANOMA

CROSS-REFERENCE TO RELATED APPLICATIONS

This application claims priority under 35 U.S.C. §119(e) to U.S. Patent Application Ser. No. 60/965,178 filed Aug. 17, 2007, which is herein incorporated by reference in its entirety.

GRANT INFORMATION

This invention was made in part with government support under NCI Grant No. CA099961 awarded by the National Institutes of Health. The United States government has certain rights in this invention.

FIELD OF THE INVENTION

This invention relates generally to compounds and methods of treatment of melanoma, and more specifically the compounds acetyl isogambogic acid and celastrol and derivatives thereof in the treatment of melanoma.

BACKGROUND OF THE INVENTION

Melanoma is a serious form of skin cancer in humans. It arises from the pigment cells (melanocytes), usually in the skin. Melanoma is currently increasing at the fastest rate of all cancers in the United States. Without even including melanoma in-situ, it is the seventh most common serious cancer in the United States. There are projected to be 60,000 new cases of melanoma in the United States in 2006, with 7,600 deaths due to melanoma. This means, on average, about one person per hour will die in the U.S. due to this disease. It is the most common cancer in women aged 25-29 years old, it is second in malignancies of adulthood in terms of life-years lost and currently the prognosis for melanoma once it is disseminated is dismal.

The growth and metastasis of melanoma as well as its notorious resistance to therapy present major obstacles to its treatment. A growing number of genetic and epigenetic changes in melanomas impact genes associated with melanocyte development and maintenance, cell cycle control, resistance to apoptosis, angiogenic and metastatic capacity. Among the genetic changes commonly found in human melanomas are mutations in protein kinases of the MAPK family, indicating that signal transduction pathways have been largely modified in this tumor type. Specifically, the prevalence of activating mutations in B-RAF and N-Ras has been largely associated with the activation of downstream targets—MEK and in many cases ERK-MAPK. Constitutive activation of these kinases results in corresponding upregulation of their targets, including genes implicated in the development and maintenance of melanoma such as MITF, iNOS and cyclin D1.

In addition to changes in the MAPK signaling pathway, other pathways are deregulated in melanoma, for reasons as yet unknown. For example, a growing fraction of melanomas is recognized as carrying an inactive form of PTEN, a protein phosphatase implicated in the regulation of AKT signaling pathways and their downstream mTOR and p70S6 effectors. Upregulation of PKC and JNK has also been observed in melanoma. Other regulatory components that are modified in melanoma include cell cycle regulatory proteins, such as cyclin-dependent kinases (CDKN2A) CDK2, p16/CDK/pRb and cyclin D1.

Modifications were also recorded in MMP, proteases associated with tumor cells metastatic capacity and chaperones such as HSP90. The anti-apoptotic proteins such as Bcl2 and the transcription factors ATF1, AP1 and ATF2 also cooperate in conferring resistance to apoptosis and metastatic capacity on melanoma. The complexity of changes that take place in melanoma are further illustrated in the rewiring of key signal transduction pathways; for example, ERK causes upregulation of c-Jun and JNK activity. The transcription factor ATF2 has been suggested as a marker and possible target for this tumor type (Berger et al., Cancer Res 63:8103-7, 2003; and Bhoumik et al., PNAS 101:4222-7, 2004). Analysis of 544 human melanomas using tissue arrays revealed that nuclear localization of ATF2 is associated with poor prognosis, thereby pointing to the possibility that constitutively active ATF2 may contribute to the development and progression of human melanomas. Consistent with this possibility, inhibition of ATF2 function by means of a 50 amino acid peptide derived from ATF2 sensitized melanoma to apoptosis (Bhoumik et al., Clin Cancer Res 7:331-42, 2001) and inhibited growth and metastasis in mouse models (Bhoumik et al., Cancer Res 64:8222-30, 2004; and Bhoumik et al., J Clin Invest 110:643-50, 2002). ATF2 peptides elicit such effects by virtue of their ability to inhibit ATF2 concomitant with an increase in JNK and consequently c-Jun activities.

SUMMARY OF THE INVENTION

The present invention is based on the finding that acetyl isogambogic acid (AIGA), celastrol (CSL), and derivatives thereof (i) induce melanoma cell death; (ii) inhibit the transcriptional activity of activating transcription factor 2 (ATF2); (iii) induce the activity of JNK and transcriptional activity of c-Jun; (iv) require active JNK for the ability to impact melanoma viability; and (v) inhibit tumorigenesis and metastasis.

Accordingly, in one aspect of the invention there are provided methods for inhibiting melanoma growth, comprising contacting the melanoma with an effective amount of celastrol or a derivative thereof. Also provided are methods of inhibiting metastasis of melanoma comprising contacting the melanoma with an effective amount of celastrol or a derivative thereof. In addition, methods for sensitizing melanoma cells to apoptosis comprising contacting the cells with an effective amount of celastrol or a derivative thereof are provided. Further, methods of treating melanoma in a subject in need thereof comprising administering an effective amount of celastrol or a derivative thereof are provided.

In another aspect of the invention, there are provided methods for inhibiting melanoma growth, comprising contacting the melanoma with an effective amount of acetyl isogambogic acid or a derivative thereof. Also provided are methods of inhibiting metastasis of melanoma comprising contacting the melanoma with an effective amount of acetyl isogambogic acid or a derivative thereof. In addition, methods for sensitizing melanoma cells to apoptosis comprising contacting the cells with an effective amount of acetyl isogambogic acid or a derivative thereof are provided. Further, methods of treating melanoma in a subject in need thereof comprising administering an effective amount of acetyl isogambogic acid or a derivative thereof are provided.

In a further aspect, the invention provides derivatives of celastrol. In certain embodiments, the derivative is an amide analogue. In other embodiments, the derivative is an ester analogue. Also provided are compositions of a celastrol derivative and a pharmaceutically acceptable carrier.

DETAILED DESCRIPTION OF THE INVENTION

Figure 1:
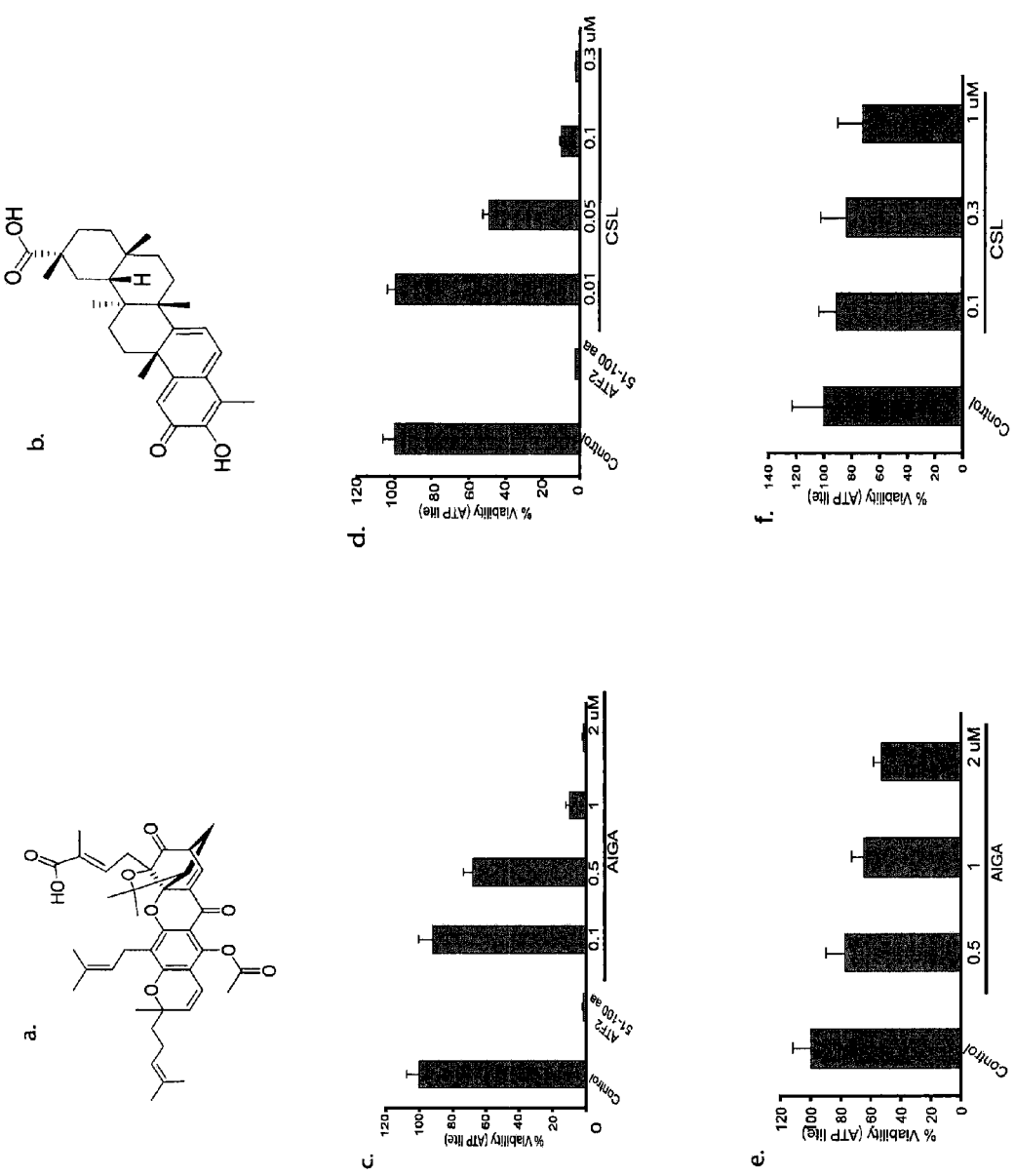
FIG. 1a shows the chemical structure of AIGA.
FIG. 1b shows the chemical structure of CSL.
FIG. 1c shows a graph of the percent viability of SW1 cells treated with ATF2 peptide ("ATF2 51-100 aa") or AIGA at the indicated concentrations.
FIG. 1d shows a graph of the percent viability of SW1 cells treated with ATF2 peptide or CSL at the indicated concentrations.
FIG. 1e shows a graph of the percent viability of normal melanocytes treated with AIGA at the indicated concentrations.
FIG. 1f shows a graph of the percent viability of normal melanocytes treated with or CSL at the indicated concentrations.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

In accordance with the present invention there are provided methods of inhibiting growth and metastasis of melanoma, methods of sensitizing melanoma cells to apoptosis, and methods of treating a subject having melanoma using acetyl isogambogic acid, celastrol, or a derivative thereof.

Acetyl isogambogic acid (AIGA), a derivative of gambogic acid, has the following structure:

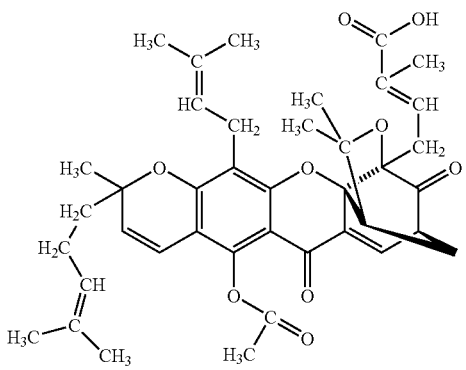

Gambogic acid, which was originally isolated from the resin of the garcinia hanburyl tree, has cytotoxic properties. In recent studies AIGA was shown to possess the capacity to potently induce apoptosis in a breast cancer cell line T47D (Zhang et al., Bioorg Med Chem 12:309-17, 2004), in a human hepatoma cell line SMMC-7721 (Guo et al., Acta Pharmacol Sin 25:769-74, 2004) and in a gastric carcinoma cell line BGC-823, in part through G2M phase arrest (Jun et al., Carcinogenesis 28:632-8, 2007). In other studies, AIGA was shown to potentiate TNF induced apoptosis in a human leukemia cell line by modulating the NFκB signaling pathway (Pandey et al., Blood 2007).

Celastrol (CSL) is a quinone methide triterpenoid and has the following structure:

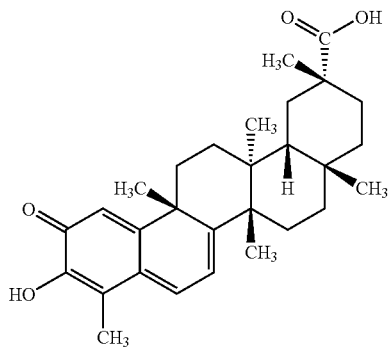

CSL was isolated from the Chinese "thunder of god vine" plant was reported to exhibit immunosuppressive activities (Zhou, Mem Inst Oswaldo Cruz 86 Suppl 2:219-26, 1991).

CSL was also shown to induce the heat shock response and to elicit cytoprotection. Consistent with these findings, gene expression signature-based chemical genomic prediction identified CSL as a modulator of the HSP90 pathway. Finally, CSL, at micromolar concentrations, was shown capable of inhibiting proteasome activity and the growth of prostate cancer cells in nude mice (Yang et al., Cancer Res 66:4758-65, 2006). In some embodiments, the invention provides derivatives of celastrol. In certain embodiments, the derivative is an amide analogue. In other embodiments, the derivative is an ester analogue. In preferred embodiments, the derivative has the structure I:

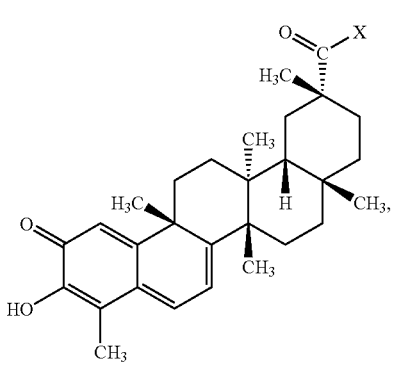

wherein X is a moiety selected from a group consisting of a —O—$C_yH_{2y+1}$, —O—Z, —O—$CH_2$—C(O)—R', and NR"R'", and wherein R' is an alkyl; and each of R" and R'" is independently selected from a group consisting of H, an alkyl, an alkenyl, an alkadienyl, a substituted alkyl, benzyl, a substituted benzyl comprising a substituent attached directly to the ring, and a 3-methylenepyridyl, or N, R" and R'" taken together form a heterocycle selected from a group consisting of pyrrolidine, morpholine, and piperazine, Z is alkenyl or alkadienyl, y is selected from the group consisting of 2, 3, 5-10, with the further proviso that in each of the —O—$C_yH_{2y+1}$, R', R" and R'", the alkyl, the alkenyl, where present, is straight-chained or branched.

The term "heteroatom" refers to any atom other than carbon, for example, N, O, or S.

The term "heterocyclic," when used to describe an aromatic ring, refers to the aromatic rings containing at least one heteroatom, as defined above.

The term "heterocyclic," when not used to describe an aromatic ring, refers to cyclic (i.e., ring-containing) groups other than aromatic groups, the cyclic group being formed by between 3 and about 14 carbon atoms and at least one heteroatom described above.

The term "substituted heterocyclic" refers, for both aromatic and non-aromatic structures, to heterocyclic groups further bearing one or more substituents described below.

The term "alkyl" refers to a monovalent straight or branched chain hydrocarbon group having from one to about 12 carbon atoms, for example, methyl, ethyl, n-propyl, iso-propyl, n-butyl, iso-butyl, tert-butyl, n-pentyl (also known as n-amyl), n-hexyl, and the like. The term "lower alkyl" refers to alkyl groups having from 1 to about 6 carbon atoms.

The term "substituted alkyl" refers to alkyl groups further bearing one or more substituents such as hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, aldehyde, acyl, oxyacyl, carboxyl, sulfonyl, sulfonamide, sulfuryl, and the like.

The term "alkenyl" refers to straight-chained or branched hydrocarbyl groups having at least one carbon-carbon double bond, and having between about 2 and about 12 carbon atoms, and the term "substituted alkenyl" refers to alkenyl groups further bearing one or more substituents described above.

The term "amide," or "amido," or "amide group," or "amido group" is defined to include moieties containing at least one acyl group >C=O attached to nitrogen. The term "substituted amide" is defined to include moieties containing a structure RNH—CO—, in which R is an organic radical.

The term "aryl" refers to aromatic groups having between about 5 and about 14 carbon atoms and the term "substituted aryl" refers to aryl groups further bearing one or more substituents described above.

The term "aralkyl" refers to an aryl or heteroaryl group, as defined herein, attached through a C1-C6 alkyl linker. Examples of "aralkyl" include, but are not limited to, benzyl, phenylpropyl, 2-pyridylmethyl, 3-isoxazolylmethyl, 2-imidazolylethyl.

The term "heteroaryl" refers to aromatic rings, where the ring structure is formed by between 3 and about 14 carbon atoms and by at least one heteroatom described above, and the term "substituted heteroaryl" refers to heteroaryl groups further bearing one or more substituents described above.

The term "alkoxy" refers to the moiety —O-alkyl, wherein alkyl is as defined above, and the term "substituted alkoxy" refers to alkoxy groups further bearing one or more substituents described above.

The term "cycloalkyl" refers to alkyl groups having between 3 and about 8 carbon atoms arranged as a ring, and the term "substituted cycloalkyl" refers to cycloalkyl groups further bearing one or more substituents described above.

The term "piperazine" is defined to refer to a 6-member saturated heterocycle having two nitrogen atoms.

The term "pyridyl" is defined to include moieties containing a radical derived from pyridine. One structure of pyridyl is shown as the structure (Py):

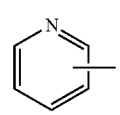

(Py)

The term "pyrrolidine" refers to a 5-member saturated heterocycle having one nitrogen atom.

The term "morpholine" refers to a 6-member saturated heterocycle having one nitrogen atom and one oxygen atom.

Some exemplary compounds described by structure I that can be used in any of the methods include, but are not limited to, the following compounds II through XV shown below:

II
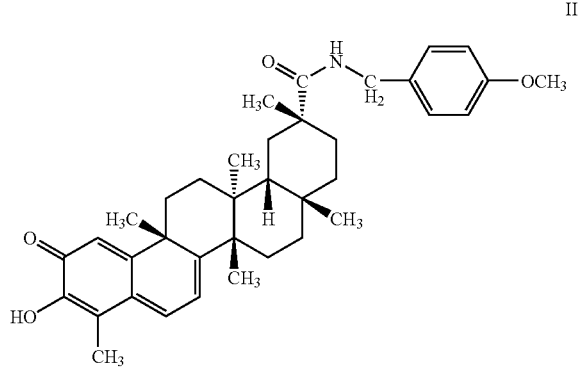
III
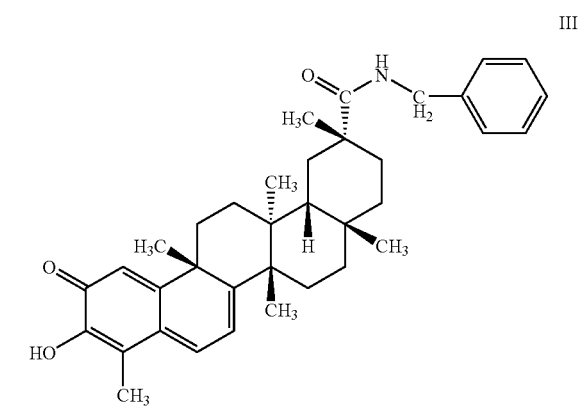
IV
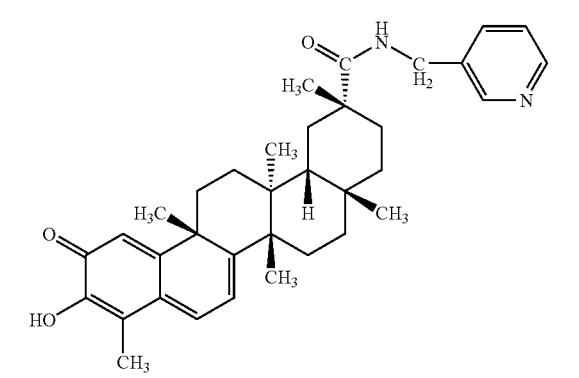
V
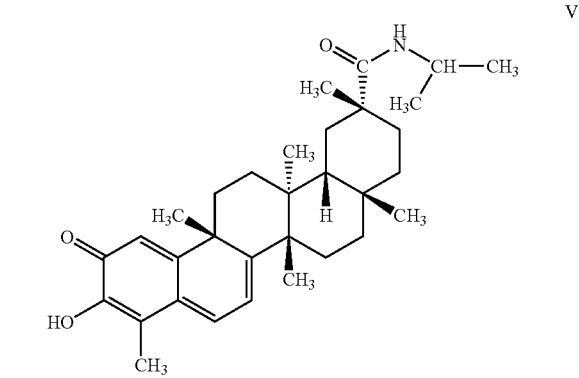
VI
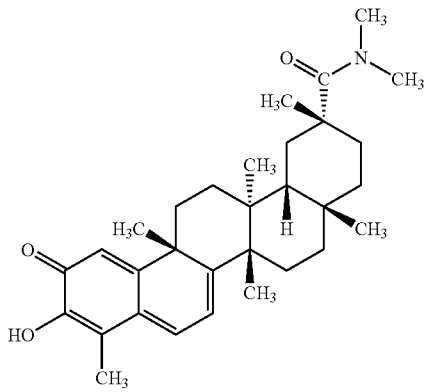
VII
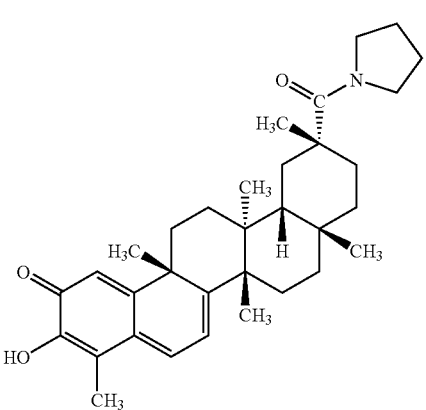
VIII
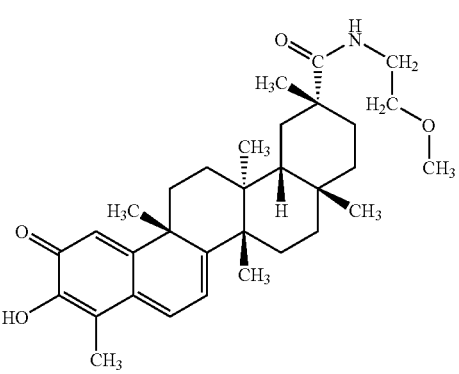
IX
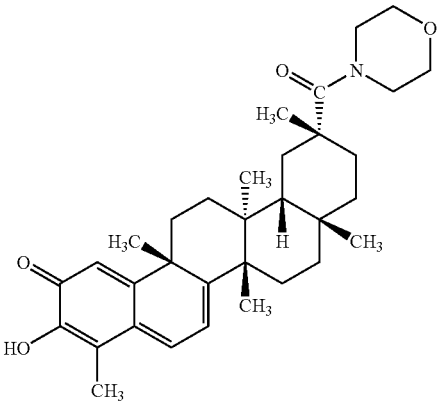

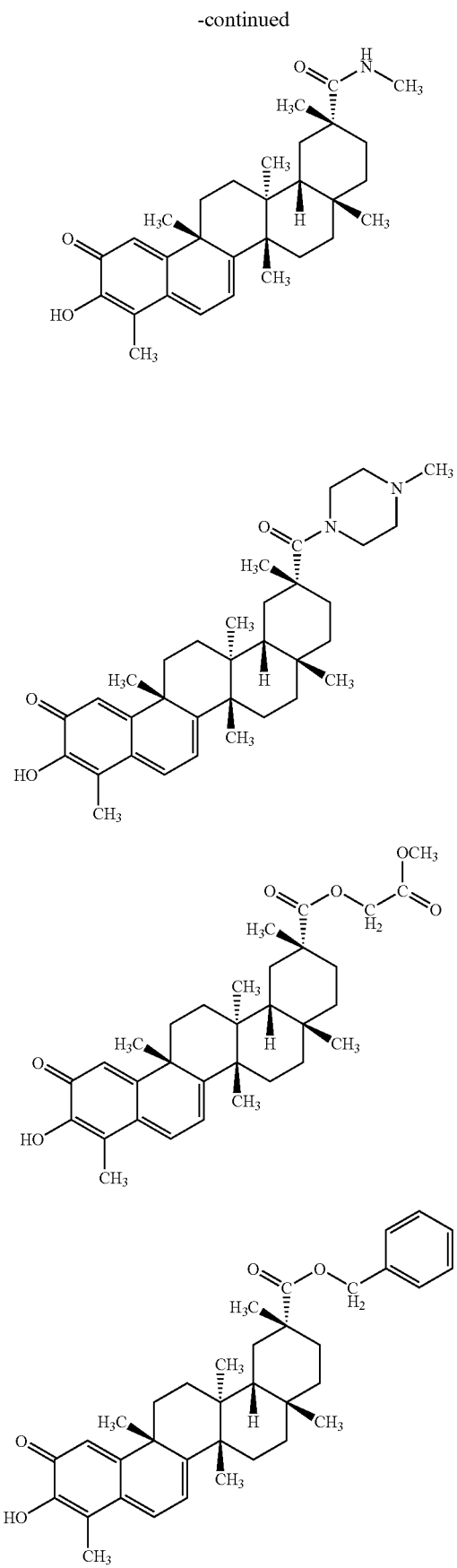

In another embodiment, there are provided pharmaceutical compositions comprising a compound according to the present invention. Thus, in one embodiment, the invention provides a pharmaceutical composition including a compound of the invention present in an amount effective to treat cancer, in particular melanoma or melanoma metastasis. In addition to a compound of the present invention, the pharmaceutical composition may also contain other therapeutic agents, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques known in the art of pharmaceutical formulation.

The term "effective amount" of a compound refers an amount that is non-toxic to a subject or a majority or normal cells, but is an amount of the compound that is sufficient to provide a desired effect (e.g., inhibition of growth of a melanoma, inhibition of metastasis of a melanoma, or sensitization of cells to apoptosis). This amount may vary from subject to subject, depending on the species, age, and physical condition of the subject, the severity of the disease that is being treated, the particular compound used, its mode of administration, and the like. Therefore, it is difficult to generalize an exact "effective amount," yet, a suitable effective amount may be determined by one of ordinary skill in the art.

The term "pharmaceutically acceptable" refers to the fact that the carrier, diluent or excipient must be compatible with the other ingredients of the formulation and not deleterious to the recipient thereof. For example, the carrier, diluent, or excipient or composition thereof may be administered to a subject along with a compound of the invention without causing any undesirable biological effects or interacting in an undesirable manner with any of the other components of the pharmaceutical composition in which it is contained.

The compounds used in the methods of the invention may be in the form of a salt, in particular, compounds having a carboxylic acid moiety (e.g., CSL). The salt is preferably a pharmaceutically acceptable salt. The term "pharmaceutically acceptable salt" includes salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, and pamoate (e.g., 1,1'-methylene-bis-(2-hydroxy-3-naphthoate)) salts. Additional pharmaceutically acceptable salts are known to those of skill in the art.

The compounds of the invention may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like.

Salts of the invention can include amine salts formed by the protonation of an amino group with inorganic acids such as hydrochloric acid, hydrobromic acid, hydroiodic acid, sulfuric acid, phosphoric acid, and the like. Salts of the invention can also include amine salts formed by the protonation of an amino group with suitable organic acids, such as p-toluenesulfonic acid, acetic acid, and the like. Additional excipients which are contemplated for use in the practice of the present invention are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs of the invention compounds are included in the present invention.

Pharmaceutical compositions of the invention may be administered by any suitable means, for example, orally, such as in the form of tablets, capsules, granules or powders; parenterally, such as by subcutaneous, intravenous, intramuscular, intrathecal, or intracisternal injection or infusion techniques (e.g., as sterile injectable aqueous or non-aqueous solutions or suspensions); or topically, such as in the form of a cream or ointment; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The pharmaceutical compositions for the administration of the compounds of this invention, either alone or in combination with other therapeutic agents, may conveniently be presented in unit dose form and may be prepared by any of the methods well known in the art of pharmacy. All methods include bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of disease. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or cosolvent or complexing agent or dispersing agent or excipient or combination thereof, for example 1,3-butanediol, polyethylene glycols, polypropylene glycols, ethanol or other alcohols, povidones, various brands of TWEEN surfactant, sodium dodecyl sulfate, sodium deoxycholate, dimethylacetamide, polysorbates, poloxamers, cyclodextrins, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the invention may be formulated in aqueous solutions, preferably in physiologically compatible buffers such as Hanks' solution, Ringer's solution, or physiologically buffered saline. For tissue or cellular administration, or particularly topical administration, penetrants appropriate to the particular barrier to be permeated are used in the formulation. Such penetrants are generally known in the art. Pharmaceutical formulations for parenteral administration include aqueous solutions of the active compounds in water-soluble form.

Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

For topical use, creams, ointments, jellies, solutions or suspensions, etc., containing the compounds of the present invention are employed.

In one aspect of the invention there are provided methods for inhibiting melanoma growth, comprising contacting the melanoma with an effective amount of celastrol or a derivative thereof. Also provided are methods of inhibiting metastasis of melanoma comprising contacting the melanoma with an effective amount of celastrol or a derivative thereof. In addition, methods for sensitizing melanoma cells to apoptosis comprising contacting the cells with an effective amount of celastrol or a derivative thereof are provided. In some embodiments, celastrol is used in these methods. In other embodiments a celastrol derivative is used, preferably the derivative is an amide analogue, more preferably the derivative is an ester analogue. In particular embodiments the derivative is pristimerin. In preferred embodiments the celastrol derivative is defined by structure I; preferred compounds according to structure I are structures II-XV. More preferred compounds include structures II, IV-VIII, and XII-XV; still more preferred compounds include structures XIII and XV. A combination of two or more of any of the above compounds may also be used.

In another aspect of the invention, there are provided methods for inhibiting melanoma growth, comprising contacting the melanoma with an effective amount of acetyl isogambogic acid or a derivative thereof. Also provided are methods of inhibiting metastasis of melanoma comprising contacting the melanoma with an effective amount of acetyl isogambogic acid or a derivative thereof. In addition, methods for sensitizing melanoma cells to apoptosis comprising contacting the cells with an effective amount of acetyl isogambogic acid or a derivative thereof are provided.

The term "inhibit" is used in reference to a baseline level of a specified activity (e.g., tumor growth or metastasis), which can be the level of the specified activity in the absence of an agent that has the inhibiting activity.

In a further aspect of the invention, there are provided methods of treating melanoma in a subject in need thereof comprising administering an effective amount of acetyl isogambogic acid (AIGA), celastrol, or a derivative thereof are provided. In some embodiments, celastrol or AIGA is used in these methods. In other embodiments a derivative of AIGA is used. In still other embodiments a celastrol derivative is used, preferably the derivative is an amide analogue, more preferably the derivative is an ester analogue. In particular embodiments the derivative is pristimerin. In preferred embodiments the celastrol derivative is defined by structure I; preferred compounds according to structure I are structures II-XV. More preferred compounds include structures II, IV-VIII, and XII-XV; still more preferred compounds include structures XIII and XV. A combination of two or more of any of the above compounds may also be used.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

In some embodiments, the present invention provides a method of ameliorating or treating a tumor in a subject with the compounds described herein. As used herein, the term "ameliorating" or "treating" means that the clinical signs and/or the symptoms associated with the cancer or melanoma are lessened as a result of the actions performed. The signs or symptoms to be monitored will be characteristic of a particular cancer or melanoma and will be well known to the skilled clinician, as will the methods for monitoring the signs and conditions. For example, the skilled clinician will know that the size or rate of growth of a tumor can monitored using a diagnostic imaging method typically used for the particular tumor (e.g., using ultrasound or magnetic resonance image (MRI) to monitor a tumor).

Treatment of a melanoma may include the treatment of solid tumors or the treatment of metastasis. "Metastasis" is a form of cancer wherein the transformed or malignant cells travel and spread the cancer from one site in the body to another. Cancer cells may metastasize through the bloodstream, through the lymphatic system, across body cavities, or any combination thereof. When melanomas have spread to the lymph nodes, micrometastases in which malignancy is only microscopic have a more favorable prognosis than macrometastases. In some cases, micrometastases may only be detected by special staining. If malignancy is only detectable by polymerase chain reaction (PCR), the prognosis is better. Macrometastases in which malignancy is clinically apparent (in some cases cancer completely replaces a node) have a far worse prognosis, and if nodes are matted or if there is extracapsular extension, the prognosis is still worse. When there is distant metastasis, the cancer is generally considered incurable. Metastases to skin and lungs have a better prognosis. Metastases to brain, bone and liver are associated with a worse prognosis.

The terms "administration" or "administering" is defined to include an act of providing a compound or pharmaceutical composition of the invention to a subject in need of treatment. The phrases "parenteral administration" and "administered parenterally" as used herein refer to modes of administration other than enteral and topical administration, and are usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration. Typically, a pharmaceutical composition of the invention will be administered topically or through subcutaneous injection at the site of the lesion.

The total amount of a compound or composition to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the compound to treat cancer in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLE 1

Identification and Characterization of Compounds with Activity in Melanoma. A high-throughput screen was performed to identify compounds that (i) induce melanoma cell death; (ii) inhibit the transcriptional activity of activating transcription factor 2 (ATF2); (iii) induce the activity of JNK and transcriptional activity of c-Jun; and (iv) require active JNK for the ability to impact melanoma viability. Two compounds were identified and newly generated derivatives were characterized in both in vitro and in vivo models.

Cell lines. Mouse melanoma (SW1) and human melanoma (LU1205) cells were maintained in DMEM supplemented with 10% FBS, L-glutamine and antibiotics. The human melanoma cell lines MEWO and WM115 were maintained in RPMI supplemented with 10% FBS and antibiotics. Primary mouse melanocytes were cultured in F-12 media supplemented with 10% FBS, antibiotics, IBMX (isobuthyl-methylxantine), bovine pituitary extract, and TPA.

Constructs and inhibitors. An ATF2 peptide (aa 51-100) was cloned into HA-tagged pcDNA3 vector as previously described (Bhoumik et al., Cancer Res 64:8222-30, 2004). 5×Jun2tk-Luc (marker for ATF2 transcriptional activities), 5×TRE-tk-Luc (marker for AP1/c-Jun transcriptional activities) and 2×NF-B-Luc were previously described (Bhoumik et al., J Clin Invest 110:643-50, 2002). Pharmacological inhibitor of JNK (SP600125) was purchased (EMD biosciences) and added (5 µM) to cultured cells as indicated in Results.

Transcriptional analysis. Transient transfection of different reporter constructs into melanoma cells was performed using LIPOFECTAMINE PLUS transfection reagent (Invitrogen). Luciferase activity was determined as previously described (Bhoumik et al., PNAS 101:4222-7, 2004).

Mitochondrial activity and apoptosis. Cells were exposed to the chemicals for 12-48 hours as indicated in Results. To measure changes in mitochondrial activity reflective of general cell viability, the ATPLITE ATP detection assay was used according to the manufacturer's recommendations (Perkin Elmer). Apoptosis analysis was performed by flow cytometry of PI-stained cells. The percentage of cells to the left of the diploid G0/1 peak, characteristic of hypodiploid cells that have partially lost DNA, was calculated as percentage of apoptotic cells (Bhoumik et al., PNAS 101:4222-7, 2004). Analysis of changes in Caspase 8 expression pattern was performed using immunoblot analysis.

Chemical Library Screen. Cells (4000) were seeded in a volume of 45 µL of media per well using a Matrix WELLMATE bulk reagent dispenser. The cells were incubated for 24 hrs @37° C. in a humidified atmosphere containing 5%

CO$_2$. Subsequently, 5 μL of 0.1 mM compounds in 10% DMSO were added to each well (final compound concentration was 0.01 mM in 1% DMSO) using a Beckman Coulter BIOMEK FX automated liquid handler. Two small molecule chemical libraries were used in the study. These libraries were the Library of Pharmacologically Active Compounds (LO-PAC1280 from Sigma-Aldrich, cat #LO1280) as well as the 2000 compounds that comprise the Spectrum Collection from Microsource Discovery Systems, Inc. Both of these libraries are comprised of small molecules that are known to be pharmacologically active. The spectrum collection not only contains 1000 small molecule compounds, but also 1000 pharmacologically active purified natural products. These libraries have previously been used for screening campaigns (Hamman et al., J Biomol Screen 7:45-55, 2002; Kocisko et al., J Virol 77:10288-94, 2003). The treated cells were incubated for 24 hrs. After incubation, 25 μL of ATPLITE 1 step (Perkin Elmer) was added to each well. ATPLITE employs a luciferase-based system to measure the relative quantity of ATP in a sample. It has been shown that ATP quantification can be used to measure cell proliferation and cytotoxicity (Kangas et al., Medical Biology 62:338-43, 1984). After the addition of ATPLITE, the plates were read using the luminescence readout of a Molecular Devices ANALYST HT multi-mode plate reader.

The celastrol (CSL) used for biological studies and to prepare amide and ester derivatives was obtained from Pay Pay Technologies (China) as a dark red crystalline solid and was used as received. For the synthesis of esters and amides all reactions were conducted in standard glassware without special regard to atmosphere or moisture. Reagents and anhydrous solvents were commercially purchased and used without purification. The purification of target compounds was performed with a Shimadzu Discovery preparative HPLC system or an ISCO COMPANION 4× flash chromatography system. Product analysis and identity confirmation was performed using a Shimadzu LC/MS and a Varian 300 MHz NMR.

Amide derivatives of celastrol were prepared as follows. Celastrol (22 mg, 0.048 mmol) in DMF (2 mL) was treated with DIEA (20 μL, 0.12 mmol), PyBOP (50 mg, 0.096 mmol), and the appropriate amine (0.05 mmol). After stirring for 20 hours at room temperature, deionized water (15 mL) was added and the mixture was extracted by ethyl acetate two times. The combined organic layers were washed with brine, dried over MgSO$_4$, and evaporated to yield a dark oil. The crude product was purified by flash chromatography (ethyl acetate:hexanes) and lyophilized to give a dark orange to red solid.

Ester derivatives of celastrol were prepared as follows. Celastrol (22 mg, 0.048 mmol) in DMF (2 mL) was treated with NaHCO$_3$ (20 mg, 0.24 mmol) and the appropriate alkyl halide (0.05 mmol). After stirring for 36 hours at room temperature, deionized water (15 mL) was added and the mixture was extracted by ethyl acetate two times. The combined organic layers were washed with brine, dried over MgSO$_4$, and evaporated to yield a dark red oil. The crude product was purified by flash chromatography (ethyl acetate:hexanes) and lyophilized to give a dark red solid.

Immunoblot analysis. Proteins prepared from cells at the indicated time points using RIPA buffer and 75 μg were separated on SDS-PAGE followed by immunoblot analysis using the antibodies indicated. Antibodies used were as follows: anti-JNK (Santa Cruz), phospho-JNK (Promega Corp.; Madison, Wis.), phospho c-Jun (Cell Signaling Technology, Inc.; Danvers, Mass.), c-Jun (Santa Cruz Biotechnology, Inc.; Santa Cruz, Calif.) and Caspase 8 (BD Biosciences; San Jose, Calif.).

Tumor growth and metastasis in vivo. GFP-expressing SW1 cells were trypsinized, resuspended in PBS, and injected subcutaneously ($1 \times 10^6$) into the lower flank of 6 to 7-week-old mice. When tumors reached a size of about 50 mm$^3$, the indicated compounds (100 μL of the vehicle—10% DMSO, 70% Cremophor/ethanol (3:1), and 20% PBS and 1.0 mg/kg of celastrol or 0.5 mg/kg of the derivatives CA16, CA19) were injected i.p. every alternate day. Body weight and tumor growth were monitored every 2 days. GFP-expressing SW1 tumors were monitored in vivo on shaved mice with a light box illuminated by blue light fiber optics (Lightools Research; Encinitas, Calif.), and imaging was carried out with a digital camera (Nikon D100). Tumors were measured for up to 3 weeks. For metastases studies, LU1205 cells ($1 \times 10^6$) were injected i.v. into the lateral tail vein of nude mice. At the end of the experiment, the lungs and tumors were excised and weighed. To detect metastatic lesions, lungs were fixed in formalin, embedded in paraffin and subjected to hematoxylin and eosin staining.

Screening for compounds that mimic the ATF2-peptide effect on melanoma cells. A chemical library of 3280 pharmacologically active small molecules (Hamman et al., J Biomol Screen 7:45-55, 2002; Kocisko et al., J Virol 77:10288-94, 2003) was screened to identify compounds that elicit the same major effects as the ATF2 peptide. The criteria for selection included: (a) the ability to elicit apoptosis of melanoma cells; (b) inhibition of ATF2 transcriptional activity; (c) increase in c-Jun transcriptional activity; and (d) dependency on JNK activity. Compounds that met all four criteria were further assessed against a panel of melanoma cultures and in syngeneic and xenograft mouse models. The screening was stepwise; thus, only compounds that met the first criterion were taken forward for further analyses to determine their effects on ATF2 and c-Jun transcriptional activities. Using this approach, 26 of the 3280 compounds (0.8%) elicited efficient apoptosis of melanoma cells, which was monitored using the ATPLITE assay. Of the twenty six compounds, only three (0.1%) affected transcriptional activities of ATF2 and c-Jun. Since one of the three compounds was an organomercurial derivative (thimerasol), it was omitted from further analysis. Thus, more extensive studies were focused on Celastrol (CSL) and Acetyl Isogambogic Acid (AIGA), the two compounds that met the initial criteria.

Characterization of CSL and AIGA effects on mouse melanoma cells. The structures of AIGA and CSL are depicted in FIG. 1a and 1b. AIGA was tested for cytotoxicity at concentrations ranging between 0.1 and 2 μM, whereas CSL was used at a concentration of 0.01 to 0.3 μM. SW1 cells or normal melanocytes were seeded on 96 well plates and 24 h late, cells were treated with the indicated concentrations of ATF2 50-100 peptide, AIGA, or CSL for 20 h. ATF2 50-100 peptide (cloned in mammalian expression vector in frame with penetratin was transfected with the aid of lipofectamine) was used as a positive control. ATP levels were used as an indicator of cell viability and were measured using the ATPLITE ATP detection assay kit. The number of surviving cells upon AIGA treatment was normalized to the number of surviving cells under the control treatment, and the normalized number was designated as the "% Viability." Results shown in FIGS. 1c-1f represent 3 experiments. Treatment of SW1 melanoma cells with 1 μM of AIGA reduced the viability of melanoma cells to 10%, (FIG. 1c). Treatment of the SW1 cells with 0.05 μM of CSL reduced the viability of melanoma cells to 50%, and 0.1 μM reduced it to 10% (FIG. 1d). These data suggest that both compounds elicit efficient cytotoxicity at a low micromolar concentration. Normal melanocytes and fibroblasts were used as a control. At the concentrations that efficiently induced cell death in melanoma cells, CSL caused minimal toxicity (10% at 0.1 µM) whereas AIGA was more toxic (40% toxicity at the dose of 0.1 µM) on normal mouse melanocytes (FIG. 1e, 1f). Neither CSL nor AIGA elicited toxic effect on human diploid fibroblasts (IMR90) or on the normal human breast cultures MCF10 (data not shown). These data suggest that CSL exhibits potent toxicity towards melanoma cultures but not towards non transformed cells.

Figure 2:
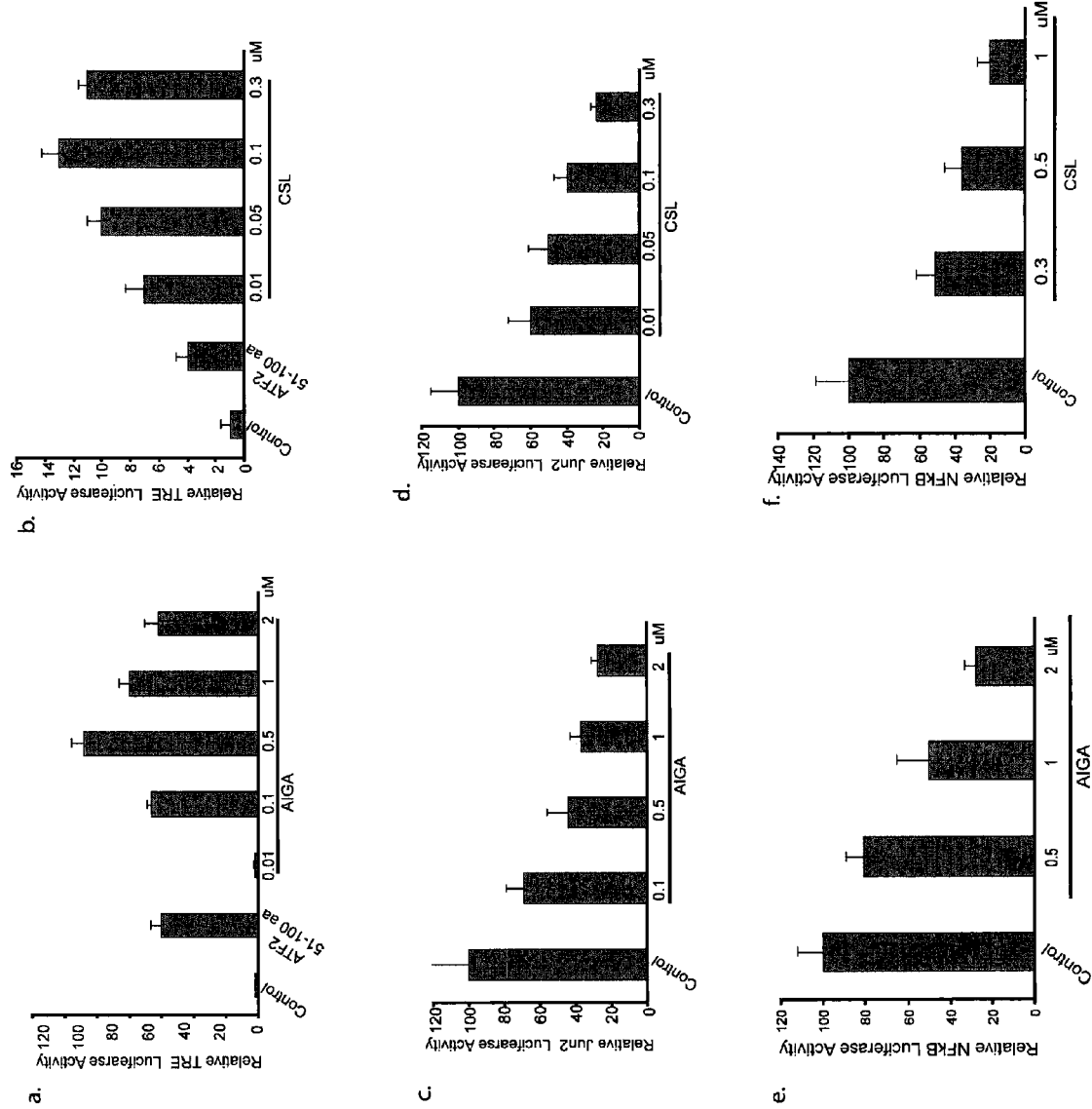
FIGS. 2a and 2b show graphs of the relative TRE luciferase activity (representing AP1/c-Jun transcriptional activity) in SW1 cells transfected with TRE-luciferase plasmid and treated with ATF2 peptide ("ATF2 51-100 aa"), AIGA (FIG. 2a) or CSL (FIG. 2b) at the indicated concentrations.
FIGS. 2c and 2d show graphs of the relative Jun2 luciferase activity (representing ATF2 transcriptional activity) in SW1 cells transfected with Jun2-luciferase plasmid and treated with AIGA (FIG. 2c), or CSL (FIG. 2d) at the indicated concentrations.
FIGS. 2e and 2f show graphs of the relative NFκ-B luciferase activity in SW1 cells transfected with NFκ-B-luciferase plasmid and treated with AIGA (FIG. 2e), or CSL (FIG. 2f) at the indicated concentrations.

The effects of the two compounds on c-Jun transcriptional activity in mouse melanoma SW1 cells was assessed. SW1 cells were transfected with the TRE-luciferase plasmid and 24 h later, cells were treated with the indicated concentrations of AIGA or CSL for 8 h before proteins were prepared and level of luciferase activity was measured. ATF250-100 peptide was used as a positive control. Data shown represent results from 3 experiments. Compared with the ATF2 peptide ("ATF2 51-100aa"), which elicits an increase in TRE-Luc, reflective of AP1/c-Jun transcriptional activity, AIGA and CSL elicited stronger activation of c-Jun transcription (FIG. 2a, 2b). AIGA induced c-Jun transcriptional activity at doses starting from 0.1 µM (FIG. 2a). Compared with AIGA, CSL was more potent in the activation of AP1/c-Jun transcription, as such activation was seen in response to treatment at doses as low as 0.01 µM (FIG. 2b).

These compounds were next assessed for their impact on ATF2 transcriptional activity. The effect of AIGA on ATF2 transcriptional activities was measured by the Jun2-luciferase assay. SW1 cells were transfected with the Jun2-luciferase plasmid and 24 h later cells were treated with the indicated concentrations of AIGA or CSL for 8 h before proteins were prepared and level of luciferase activity was measured. ATF2 51-100 peptide was used as a positive control. Data shown represent results from 3 experiments. About 0.5 µM of AIGA or 0.05 µM of CSL was required to cause about 50% inhibition of ATF2 transcriptional activity, monitored using a Jun2-Luc construct (FIG. 2c, 2d). These data reveal that, similar to the changes seen after treatment with the ATF2 peptide, both compounds effectively alter the transcriptional activities of ATF2 and c-Jun, although CSL appears to be more potent compared with AIGA.

To assess whether CSL may affect the transcriptional activities of genes other than ATF2 and c-Jun, possible changes in transcriptional activities of NF-κB were monitored. Transcriptional activation of NFκ-B was assessed using the 2-NFκ-B-luciferase assay. Briefly, SW1 cells were transfected with the 2-NFκ-B-luciferase plasmid and 24 h later, cells were treated with the indicated concentrations of AIGA or CSL for 8 h before proteins were prepared and level of luciferase activity was measured. ATF250-100 peptide was used as a positive control. Data shown represent results from 2 experiments. Addition of either AIGA or CSL causes dose-dependent inhibition of NF-κB transcriptional activity, measured by the corresponding luciferase reporter construct (FIG. 2e, 2f). These finding are consistent with earlier reports regarding the effect of CSL on the transcriptional activities of NFκB in HeLa cells.

Figure 3:
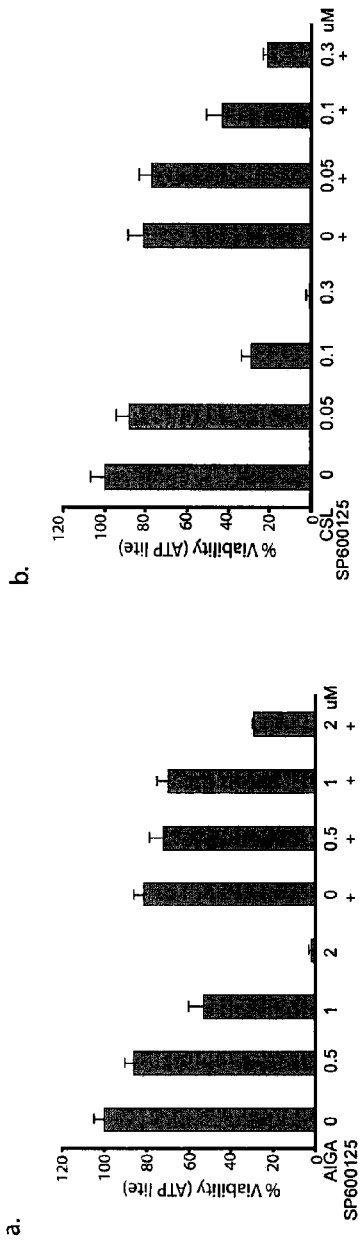
FIGS. 3a and 3b show graphs of the percent viability of SW1 cells with or without pretreatment with the JNK inhibitor SP600125 (10 μM) followed by addition of AIGA (FIG. 3a) or CSL (FIG. 3b) at the indicated concentrations for 20 h.

Several reports revealed that JNK activity is important for the ATF2 peptide's ability to elicit its effect on melanoma cells in culture and in vivo (inhibition of tumorigenicity). Thus, the two compounds were evaluated to determine if they require JNK activity for their effects on melanoma cells. To this end, the ability of AIGA or CSL to affect the viability of melanoma cells in the presence of a JNK inhibitor was tested. SW1 cells, with or without a 30-minute pretreatment with the JNK inhibitor SP600125 (10 µM), were contacted with AIGA or CSL at the indicated concentrations for 20 h. ATP levels were used to measure the cell viability using the ATPLITE kit. The number of surviving cells upon AIGA or CSL treatment was normalized to the number of surviving cells under the control treatment, and the normalized number was designated as the "% Viability." Shown are representative results from 2 experiments. Inhibition of JNK activity by the pharmacological inhibitor SP600125, attenuated the ability of AIGA or CSL to elicit the cell death of melanoma cells (FIG. 3a, 3b). Of note, inhibition of JNK activity was more pronounced at lower concentrations of CSL compared with AIGA. These findings suggest that AIGA and CSL require JNK activity to reduce the survival of melanoma cells. To assess whether these compounds affect JNK activity, changes in JNK phosphorylation on residues 183/185, which are required for its kinase activity, were monitored. Western blot analysis for JNK phosphorylation on residues 183/185 was performed on protein extracts that were prepared from cells treated with AIGA at concentrations of 0.5 µM, 1.0 µM, and 2.0 µM and a control with no AIGA treatment. Duplicate samples were treated with JNK inhibitor (SP600125). Total level of JNK was analyzed in parallel. Western blot analysis for JNK phosphorylation on residues 183/185 was performed on protein extracts that were prepared from cells treated with CSL at concentrations of 0.5 µM, 1.0 µM, and 2.0 µM and a control with no CSL treatment, as well as duplicate samples treated with JNK inhibitor. Both AIGA and CSL induced phosphorylation of JNK on these residues, which was reduced upon addition of the JNK inhibitor (SP600125), as was seen in the blots in which the bands corresponding to phosphorylated JNK in the presence of inhibitor were much lower in intensity than the bands in the absence of inhibitor for all concentrations of CSL and AIGA and was most pronounced at 1.0 M and 2.0 µM CSL or AIGA. Total JNK protein was constant.

The activation of JNK by both compounds was confirmed upon analysis of its substrate c-Jun. SW1 cells were pretreated with the JNK inhibitor SP600125 followed by addition of AIGA (0.5 µM or 2.0 µM) or CSL (0.5 µM or 1.0 µM) for 20 h. Total protein extracts were used to determine the phosphorylation of c-Jun. Both compounds efficiently induced c-Jun phosphorylation, with CSL being more potent, as seen by Western analysis using an antibody to phosphorylated c-Jun, in which the intensity of the bands corresponding to phosphorylated c-Jun increased in the presence of AIGA or CSL. These data indicate that CSL and AIGA induce JNK activity, which in turn results in the activation of its substrate c-Jun, while attenuating the degree of ATF2 transcriptional activity.

Figure 4:
FIGS. 4a and 4b show graphs of the percent apoptosis in mouse melanoma SW1 cells treated with AIGA (FIG. 4a) or CSL (FIG. 4b) at the indicated concentrations.

The finding that CSL and AIGA reduced cell viability in melanoma was made using the ATPLITE assay, which monitors the degree of mitochondrial ATP release, a marker for mitochondrial activity. To directly assess possible changes in the apoptosis of melanoma cells following their exposure to CSL or AIGA, FACS analysis of the melanoma cells was performed 48 h after treatment. Addition of AIGA or CSL to SW1 melanoma cells induced programmed cell death, with CSL exhibiting a more efficient effect. Treatment with 1 µM AIGA caused 15% apoptosis in these melanoma cultures (FIG. 4a). Treatment with CSL caused 13% apoptosis at a dose of 0.5 µM and 35% apoptosis at a dose of 1 µM (FIG. 4b). Consistent with these finding is the activation of caspases 8, a classic marker for apoptosis, which was observed upon addition of these compounds, by Western blot analysis. SW1 cells were treated with 0.5 µM AIGA, 0.5 µM CSL, 1.0 µM CSL for 24 hours. Staurosporin was used as a positive control. Immunoblot analysis using caspase 8 antibody monitored full length and cleaved forms (active) of caspase 8. β-actin was used as a loading control. The resulting immunoblots showed an increase in intensity of the cleaved forms caspase 8.

Figure 5:
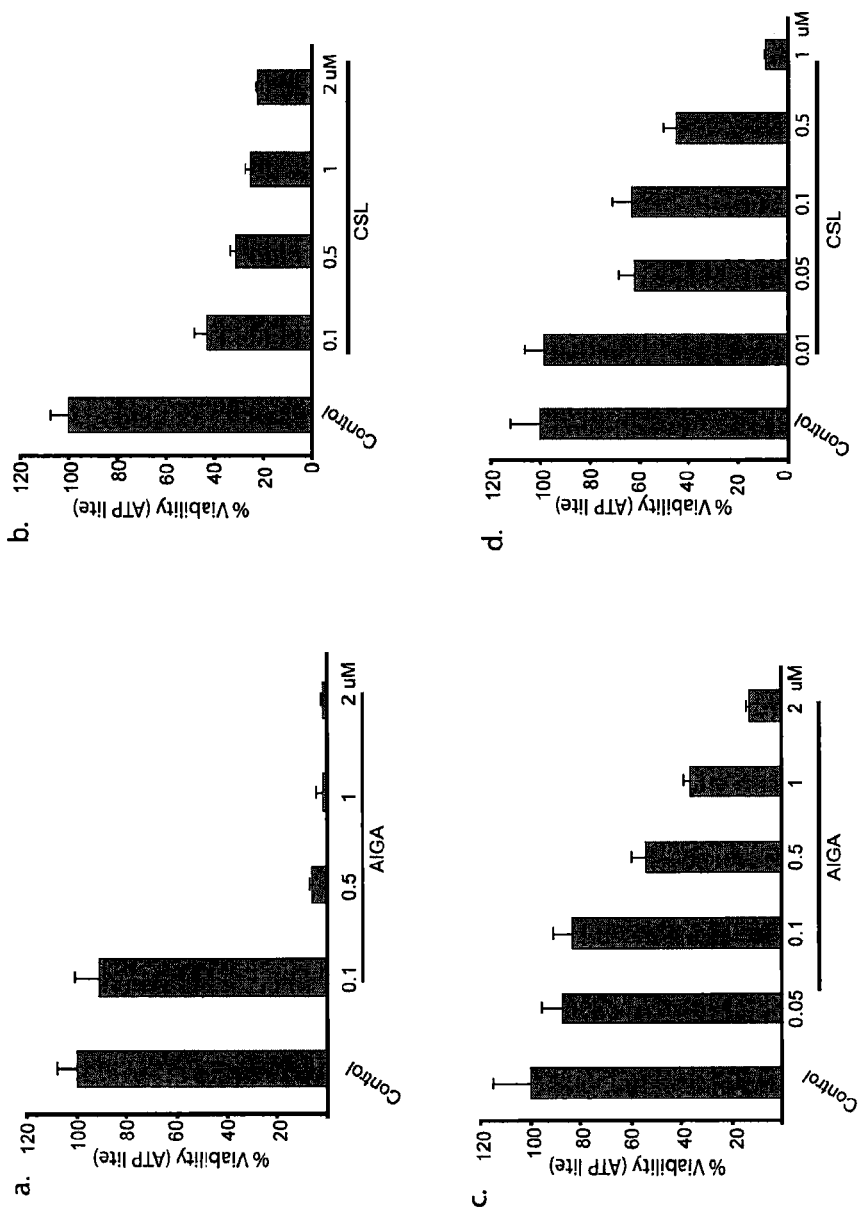
FIGS. 5a and 5b show graphs depicting the percent viability of human melanoma WM115 cells treated with AIGA (FIG. 5a) or CSL (FIG. 5b) at the indicated concentrations.
FIGS. 5c and 5d show graphs depicting the percent viability of human melanoma MeWO cells treated with AIGA (FIG. 5c) or CSL (FIG. 5d) at the indicated concentrations.

The effects of CSL and AIGA on the human melanoma cell lines WM115 and MEWO were assessed. AIGA reduced the viability of the human melanoma cultures when added at a concentration of 0.5-2 µM (FIG. 5a and FIG. 5c) whereas CSL reduced their viability at a concentration of 0.1 µM-2 µM in WM115 cells (FIG. 5b) and 0.05 µM-2 µM in MeWO cells (FIG. 5d). These data reveal that similar to their effect on the mouse melanoma cells, AIGA and CSL efficiently reduced viability of human melanoma cells.

Given the greater potency of CSL, compared with AIGA, on transcription and cell death we have devoted efforts to further optimize the ability CSL to elicit melanoma cell death. To this end, medicinal chemistry was initiated with the dual goals of (a) understanding the key structural features in CSL which impact it's apoptotic activity, and (b) identifying analogues of CSL which possess an improved pharmacological profile compared with the parent compound. First, two commercially available analogues of CSL, a CSL methyl ester (pristimerin) and dihydrocelastrol, a reduced variant of CSL that lacks the quinone methide moiety of the parent compound. Pristimerin was equipotent or even slightly more potent than celastrol (see Table 1) against SW1 cells. This finding suggests that the acidic proton present in CSL is not required for its ability to induce apoptosis in these cells.

Dihydrocelastrol, however, was inactive in the assay, suggesting that the quinone methide moiety in CSL is crucial for apoptotic activity. Thus, a series of derivatives focused on modification of the carboxylic acid moiety in CSL were synthesized. Amide derivatives (termed CA01-CA08, CA13, CA14) were synthesized and tested in the cellular assays as shown in Table 1. This set of amides were designed to interrogate both the steric and electronic requirements of the carboxylate substitute needed for optimal cellular activity. The derivatives revealed some intriguing preliminary structure-activity relationship (SAR) data (Table 1). The 4-methoxybenzyl amide (CA01) and the pyridin-3-ylmethanamine amide (CA03) were active in SW1 cells while the unsubstituted benzyl amide (CA02) was inactive. Among the aliphatic amides the isopropyl amide (CA04), the dimethyl amide (CA05), the pyrrolidine amide (CA06) and the methoxyethylamine (CA07) were all active in SW1 cells. The morpholine amide (CA08) and the N-methylpiperazine amide (CA14) were both inactive however. Surprisingly, considering the dimethyl amide (CA05) result, the monomethyl amide (CA13) was also inactive (Table 1). This suggested that the presence of an amide N—H reduces cellular activity in this series. A series of ester analogues was then synthesized, based on the rationale that, unlike primary amides, esters lack a heteroatom proton. Thus, the methyl 2-hydroxyacetate ester (CA15), the benzyl ester (CA16), the ethyl ester (CA18), and the isopropyl ester (CA19) were prepared and the cellular assay data are shown in Table 1. Among these four derivatives, two (CA16 and CA19) potently exhibited the ability to induce melanoma cell death. CA18 was not that efficient in the SW1 melanoma cells compared to CA19. Remarkably, the benzyl ester (CA16) was quite potent compared with the corresponding amide derivative (CA02) which was inactive. Taken together, these results suggest that the ester derivatives are more potent than the corresponding amide derivatives. Based on these data the CA16 and CA19 derivatives were selected as representatives for further assessment in the syngeneic and xenograft mouse models.

TABLE 1

Activity of Celastrol and Celastrol Derivatives

| Code | Compound Structure No. | Activity or $EC_{50}$ (µM) in SW1 cells | Activity or $EC_{50}$ (µM) in WM115 cells | Activity or $EC_{50}$ (µM) in WM793 cells |
|---|---|---|---|---|
| Celastrol |  | ~0.1 | active at 2 µM | active at 2 µM |
| Pristimerin |  | <0.1 | ND | ND |
| Dihydrocelastrol |  | inactive | ND | ND |
| CA01 | II | active at 0.3 µM | active at 2 µM | active at 1 µM |
| CA02 | III | inactive | inactive | inactive |
| CA03 | IV | active at 0.3 µM | Inactive | inactive |
| CA04 | V | active at 0.3 µM | active at 2 µM | inactive |
| CA05 | VI | active at 0.3 µM | active at 0.5 µM | inactive |
| CA06 | VII | active at 0.3 µM | active at 2 µM | active at 0.5 µM |
| CA07 | VIII | active at 0.3 µM | inactive | active at 2 µM |
| CA08 | IX | inactive | inactive | inactive |
| CA13 | X | Inactive | inactive | inactive |
| CA14 | XI | Inactive | inactive | inactive |
| CA15 | XII | Inactive | active at 2 µM | active at 1 µM |
| CA16 | XIII | active at 0.3 µM | active at 0.5 µM | active at 0.5 µM |
| CA18 | XIV | active at 1 µM* | active at 2 µM* | active at 1 µM* |
| CA19 | XV | active at 0.3 µM | active at 1 µM | active at 1 µM* |

Active = >50% inhibition of melanoma cell viability;
ND = Not Determined;
SW1 = mouse melanoma cells;
WM115 and WM793 = human melanoma cell lines;
*represents single analysis.

Figure 6:
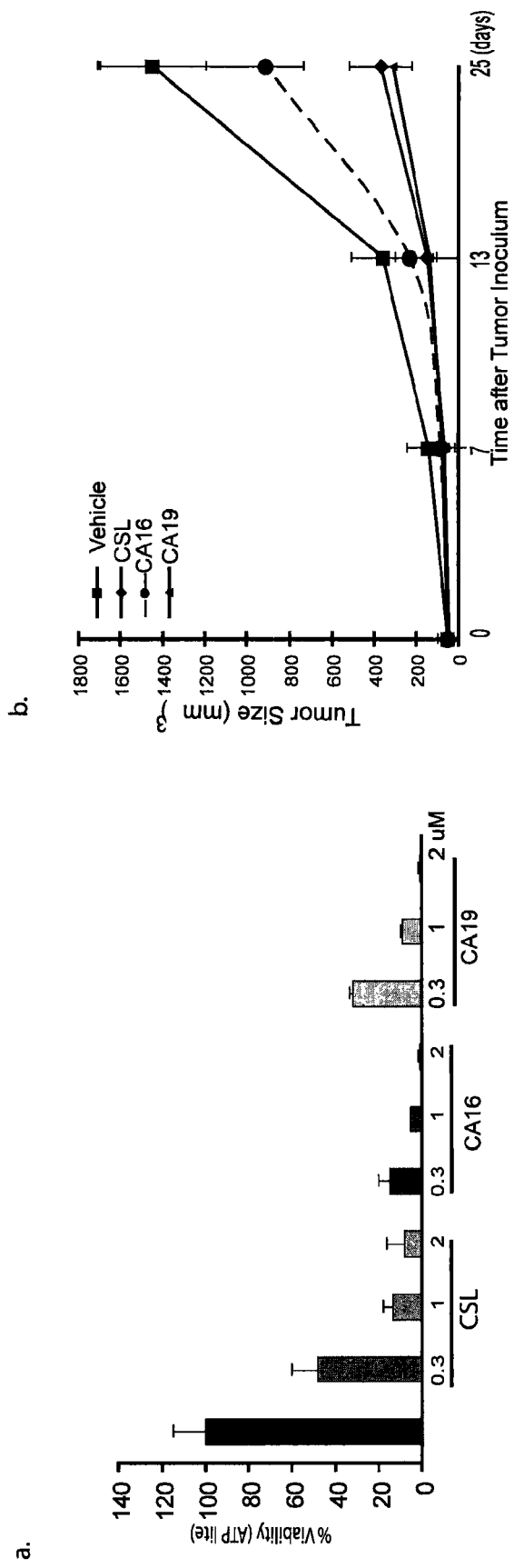
FIG. 6a shows a graph depicting the percent viability of SW1 cells treated with CSL or CSL derivatives CA16 or CA19.
FIG. 6b shows a plot of the change in size of tumors over time in C3H mice treated with vehicle, CSL, or CSL derivatives CA16 or CA19.
Figure 7:
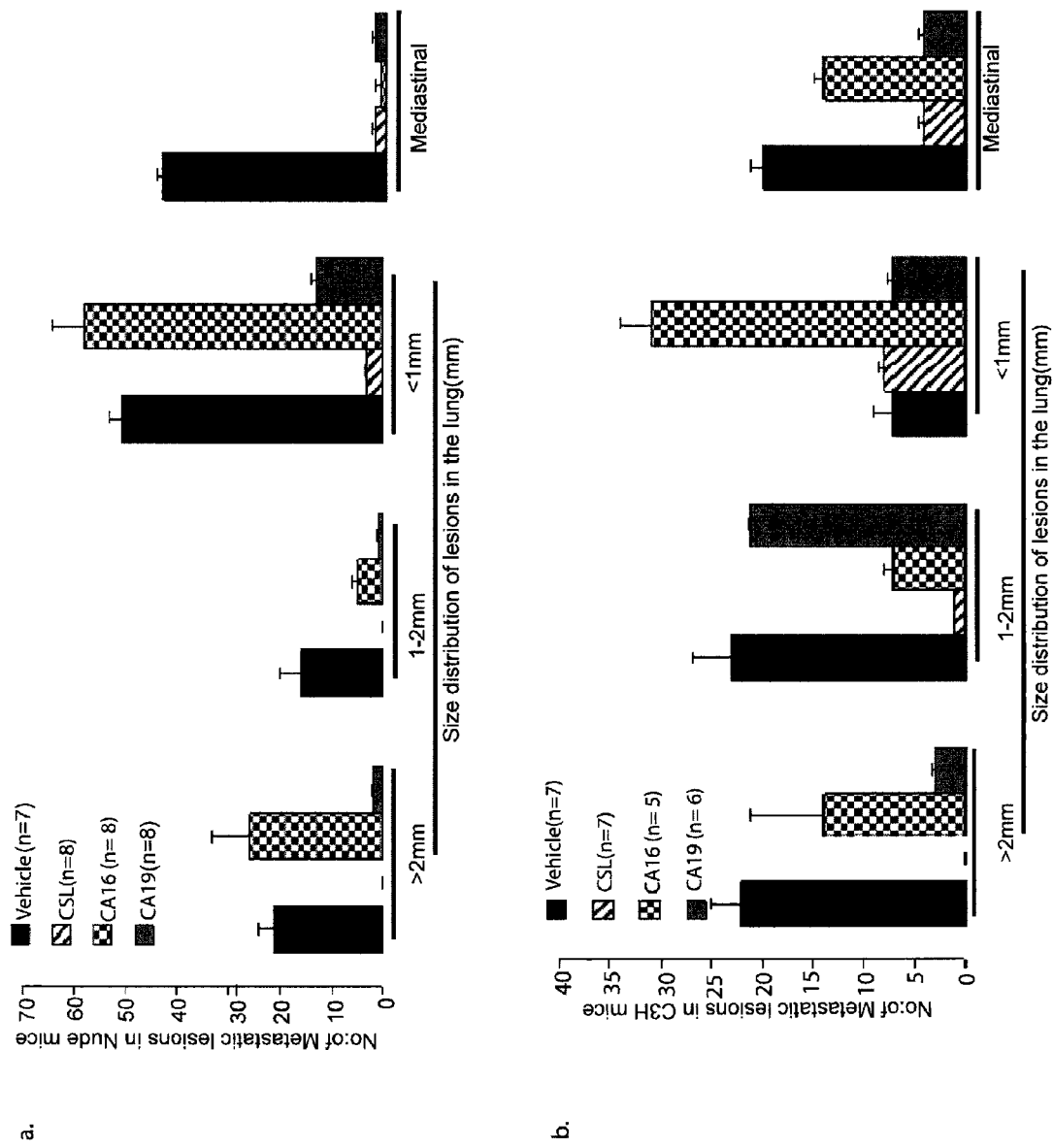
FIGS. 7a and 7b show graphs depicting the number and size of lung lesions in nude mice (FIG. 7a) or C3H mice (FIG. 7b) following injection of human melanoma LU1205 cells and treatment with vehicle, CSL, CA16 or CA19.

To assess the ability of CSL and CSL derivatives to affect the tumorigenicity and metastasis of melanoma, the mouse SW1 cell lines were used in syngeneic models. Injection of SW1 melanoma cells subcutaneously into C3H mice was followed by daily injections of CSL intraperitoneally (IP). Importantly, daily administration of CSL, CA16 or CA19 to mice at doses up to 1 mg/kg did not result in toxicity or any noticeable discomfort, indicating that these compounds are well tolerated and not toxic at these high doses. Significantly, CSL attenuated the growth of both mouse and human melanoma cells in vivo, using immune-competent and immune-deficient mouse models (FIG. 6, FIG. 7). Comparison of CSL, CA16 and CA19 for their effects on the viability of SW1 cells in culture revealed that both derivatives were as potent as the parent CSL compound (FIG. 6a). Administration of these compounds, compared with vehicle control, revealed that both CSL and the derivatives attenuated growth of SW1 tumors in mice (FIG. 6b), Briefly, SW1 cells that stably express GFP were injected s.c into C3H mice. When the tumor reached the size of 50 $mM^3$, the vehicle, CSL (1 mg/kg), CA16 (0.5 mg/kg) or CA19 (0.5 mg/kg) were administered i.p, every second day for a period of 24 days. Tumor size was measured at the indicated times. Data presented in FIG. 6b represents two experiments. Interestingly, CSL and CA19 were equally potent and reduced tumor growth 5-fold, CA16 was less effective in inhibiting tumor size (about 50% decrease) (FIG. 6b). These data suggest that CSL and its derivatives efficiently reduce melanoma tumor growth in a syngeneic mouse model.

The effect of CSL and CSL derivatives, CA16 and CA19, on the metastatic capacity of melanoma cells was then determined. Human melanoma LU1205 cells were injected into the tail vein of nude mice, followed by administration of the compounds every second day. This approach allows monitoring of changes in the number of lesions formed on the lungs, a primary organ for tumor cell growth under this experimental approach. Analysis performed 60 days following injection determined changes in the number and size of metastatic lesions in each of the experimental groups. Significantly, CSL and CA19 were efficient in inhibiting growth of large medium and small sized lesions in the lungs (FIG. 7a). CA16 had no impact on the development of the large lesions, although some activity was observed for 1-2 mm and for mediastinal lesions (FIG. 7a). These data suggest that the compounds are capable of inhibiting metastasis of human melanoma cells in a nude mouse model, and that at least one of the two derivatives tested here, CA19, exhibits potent activity that is comparable with CSL.

To further assess the impact of these compounds on the development of metastatic lesions, the SW1 mouse melanoma model using the syngeneic C3H strain was employed. Subcutaneous injection of SW1 cells results in tumor formation at the site of injection followed by metastasis to different sites within 6-8 weeks. Similar to what was observed with the human melanoma cells in the nude mice model, CSL and CA19 potently exhibit the ability to inhibit large as well as small metastatic lesions, with the exception of the 1-2 mm range (FIG. 7b) while CA16 was somewhat active it elicited an opposite effect on the development of small sized lesions (FIG. 7b). The fluctuations seen with CA16 could suggest that its activity may be limited due to stability or permeability. These data provide important support for the ability to attenuate tumorigenicity and metastatic lesion formation in melanoma xenograft and syngenic models using CSL and its isopropyl ester derivative CA19.

The present study extends other reports that documented the ability of the ATF2 peptide to cause apoptosis in mouse and human melanoma cells in culture and in animal models. To identify compounds that mimic the activity of the ATF2 peptide, a small molecule chemical library consisting of 3280 compounds was screened. Two compounds, CSL and AIGA, at low micromolar concentrations, were able to (i) induce melanoma cell death; (ii) inhibit the transcriptional activity of ATF2; (iii) induce the activity of JNK and transcriptional activity of c-Jun; and (iv) required active JNK for their ability to impact melanoma viability.

As demonstrated herein, AIGA elicits potent inhibition of melanoma cell growth in culture. Furthermore, AIGA elicits these effects in part through activation of JNK and c-Jun and inhibition of ATF2. CSL, at the concentrations used in the present studies (0.3-1 µM), did not affect the stability of short-lived proteins, including Mdm2 and p53 (data not shown). CSL was also shown to inhibit NF-κB activation through the inhibition of IKB kinase and TAK1 activities. Other studies demonstrated that NF-κB inhibits JNK activities and that inhibition of NF-κB results in elevated JNK activities. Thus, it is likely that the ability of CSL to attenuate NF-κB activity would result in increased JNK activity, which is consistent the findings herein. It is the increase in JNK activity, and consequently of its substrate c-Jun, in concert with inhibition of ATF2 activities that brings about the potent cytotoxic effects of both CSL and AIGA on melanoma cells, similar to what was previously shown for the ATF2 peptides.

Of the celastrol derivative tested, dihydrocelastrol, which lacks the quinone methide moiety, is inactive in the cellular assays (Table 1), suggesting that the quinone methide functional group of celastrol (which is absent in dihydrocelastrol) was responsible for its cytotoxic activity. While not wishing to be bound to a mechanism, the highly electrophilic nature of the quinone methide unit could potentially lead to irreversible or pseudo-irreversible binding to proteins, possibly through interaction with cysteinyl residues. On the other hand, the methyl ester derivative of CSL (pristimerin) is equally efficacious as CSL with respect to its ability to induce apoptosis, suggesting that the presence of the acidic carboxylate functional group in CSL is not required for apoptotic activity. Data recently reported by Morimoto and coworkers supports this hypothesis and further suggests that the carboxylic acid moiety in CSL is responsible for the chemical chaperone activity observed in their experiments.

A series of CSL analogues was synthesized in which the carboxylic acid unit in CSL was converted to an amide or ester derivative (see Table 1). Consistent with a role for the quinone methide unit in the cytotoxicity of CSL, some of the CSL derivatives exhibited improved efficacy (see Table 1). These results led to the identification of the benzyl ester (CA16) and isopropyl ester (CA19) derivatives as potent inducers of apoptosis which were profiled in detail in in vivo models of melanoma. The precise role for the carboxylic acid moiety in this modality of CSL remains to be further elucidated, however. Consistent with its ability to induce apoptosis of melanoma cells in culture is the ability of CSL and its isopropyl ester derivative CA19 to attenuate the growth of melanoma in mouse models. The studies reported herein performed in syngeneic mouse (SW1 cells in C3H mice) and human xenograft (LU1205 in nude mice) models demonstrate the ability of these compounds to attenuate growth of metastatic lesions, which are the major clinical burden in treatment of this tumor type. The lower activity of CA16 compared with CA19 and CSL on tumor growth and metastasis development may be attributed to stability or permeability of this compound in vivo. Along these lines, in all cases it was necessary to inject the compounds at high frequency; it is expected that improved formulation will allow prolonged half-life and more efficient delivery of these compound. The low concentrations of the compounds used in our present studies would be expected to minimize effect on other organs, consistent with our initial MTD studies. In conclusion, the effects of AIGA and CSL on melanoma cells in culture and in mouse models points to possible new treatment modalities for melanoma. In light of the notion that MAPK signaling is upregulated in human melanoma, in many cases as a result of mutations in B-RAF or N-RAS, our findings suggest that these compounds could be also considered as a means of complementing the activities of pharmacological inhibitors developed against MEK.

Although the invention has been described with reference to the above example, it will be understood that modifications and variations are encompassed within the spirit and scope of the invention. Accordingly, the invention is limited only by the following claims.

What is claimed is:

1. A method for inhibiting melanoma growth, comprising contacting the melanoma with an effective amount of a celastrol derivative, wherein the celastrol derivative is selected from the group consisting of compounds II, IV-VIII, and XII-XV:

II
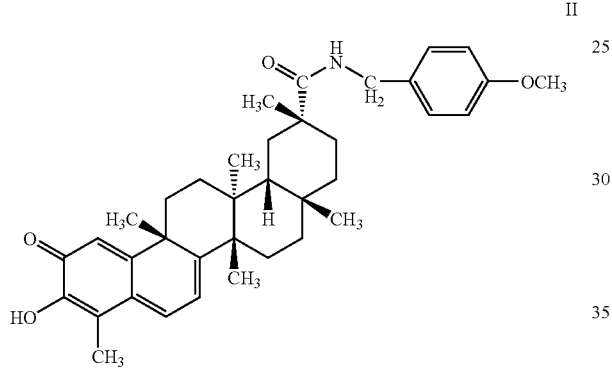

IV
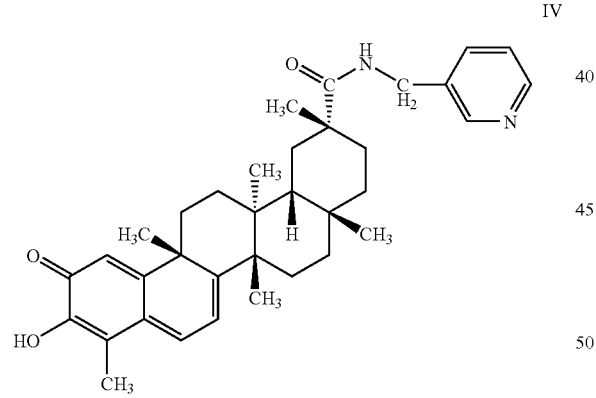

V
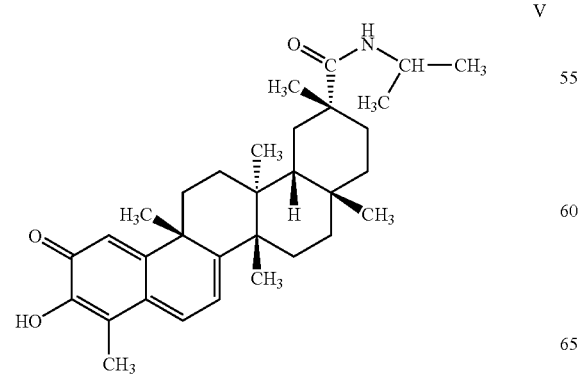

-continued

VI
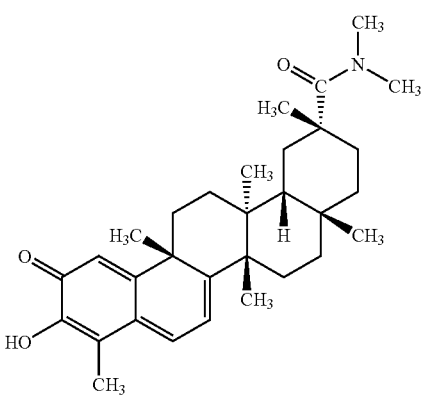

VII
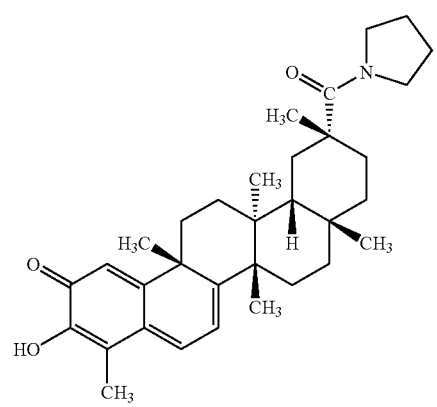

VIII
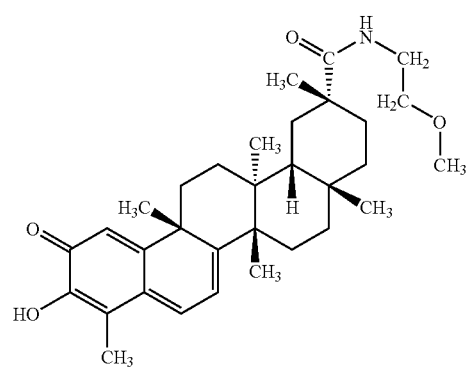

XII
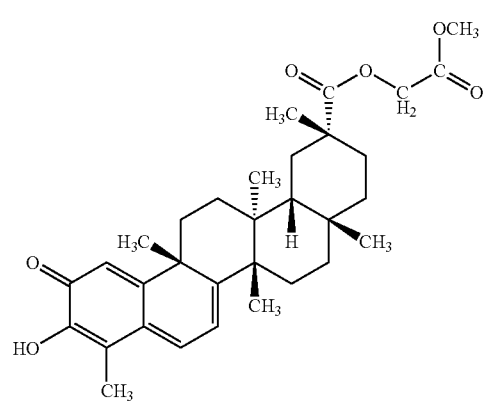

-continued

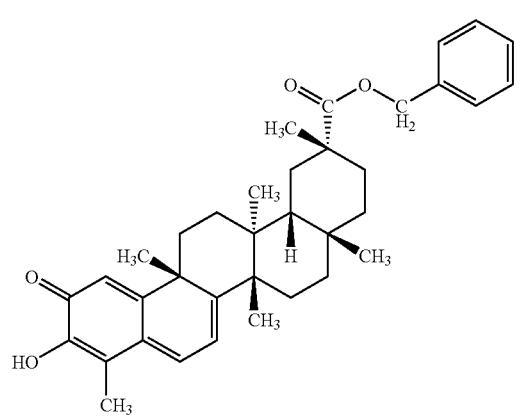
XIII

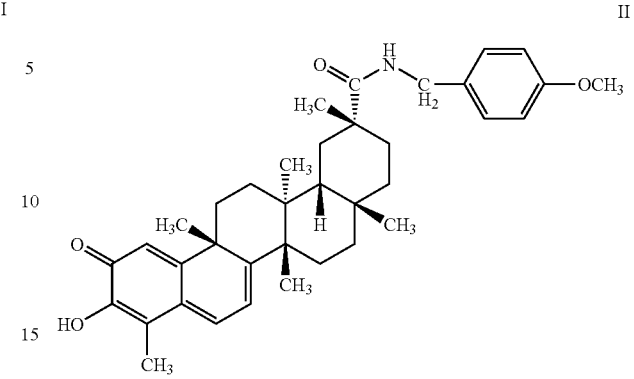
II

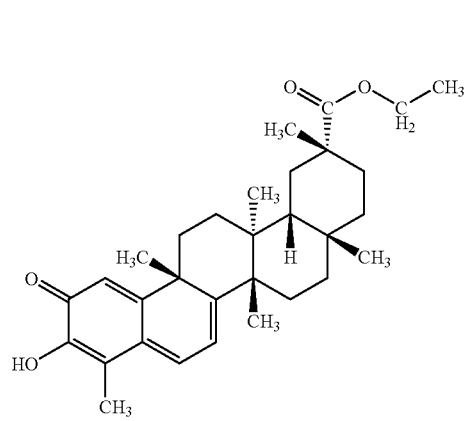
XIV

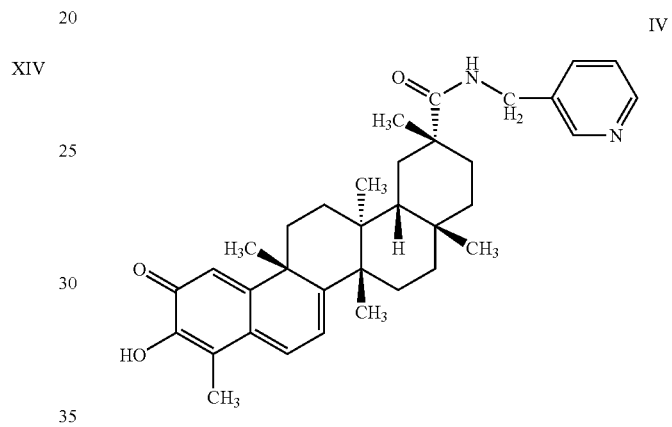
IV

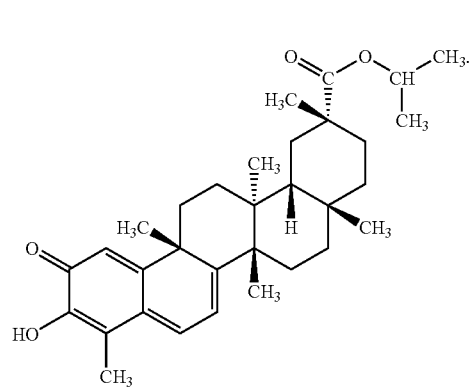
XV

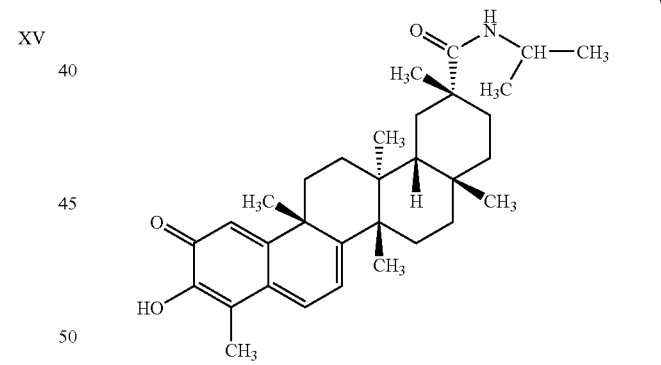
V

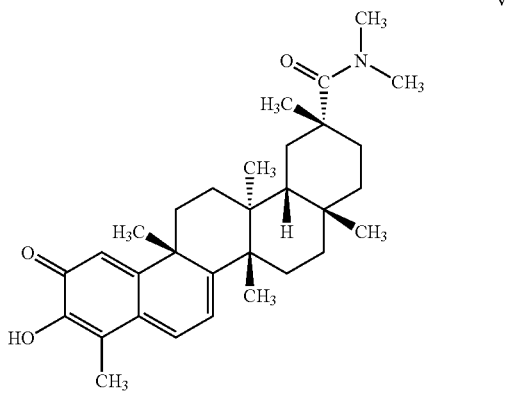
VI

2. The method of claim 1, wherein the celastrol derivative is selected from the group consisting of compounds XIII and XV.

3. The method of claim 1, wherein the contacting is via topical administration or subcutaneous administration.

4. The method of claim 1, wherein the celastrol derivative is formulated in a pharmaceutical composition.

5. A method for inhibiting melanoma metastasis comprising contacting the melanoma with an effective amount of a celastrol derivative, wherein the celastrol derivative is selected from the group consisting of compounds II, IV-VIII, XII-XV:

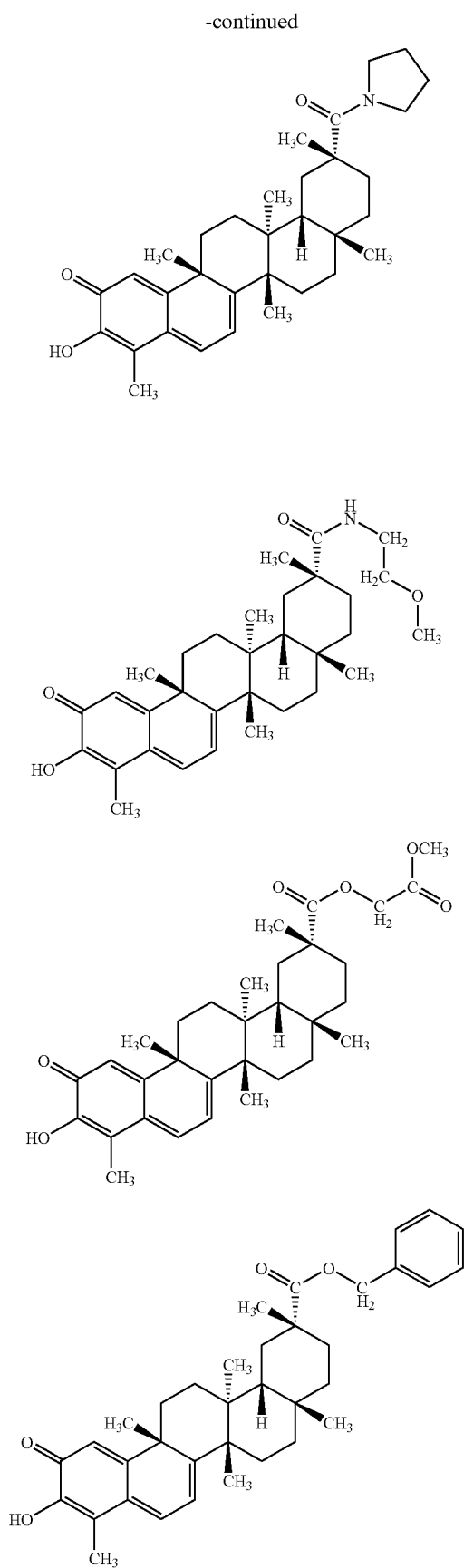
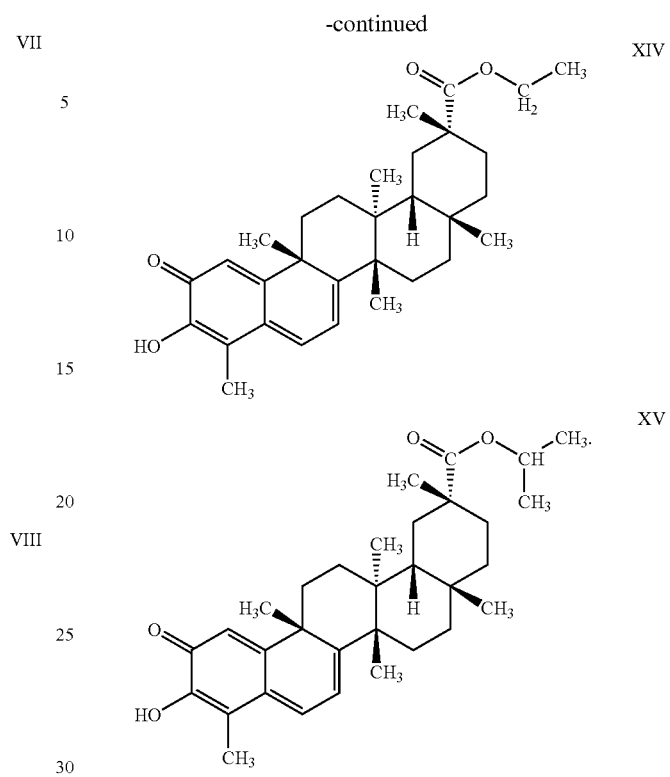
6. The method of claim 5, wherein the celastrol derivative is selected from the group consisting of compounds XIII and XV.
7. A method of sensitizing melanoma cells to apoptosis comprising contacting the cells with an effective amount of a celastrol derivative, wherein the celastrol derivative is selected from the group consisting of compounds II, IV-VIII, XII-XV:

V
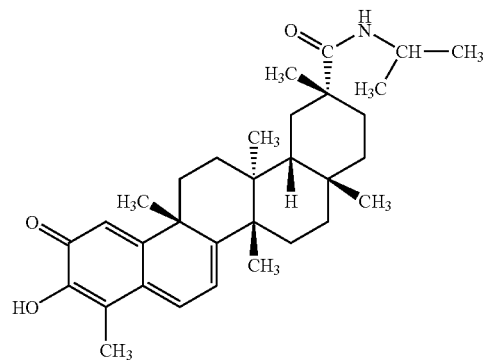
VI
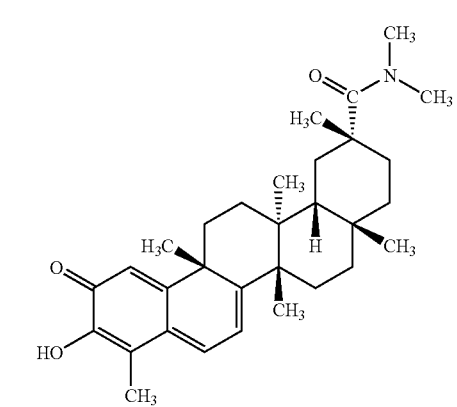
VII
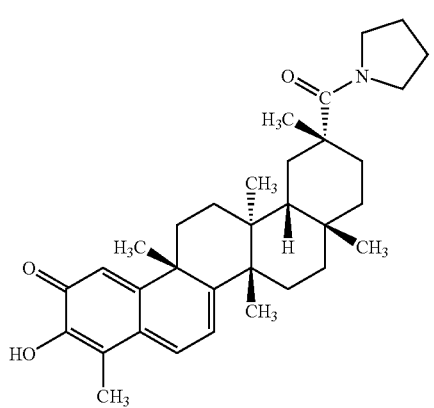
VIII
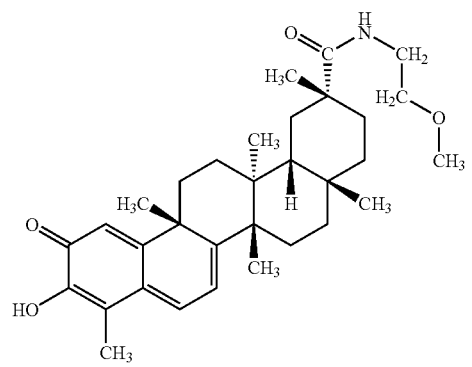
XII
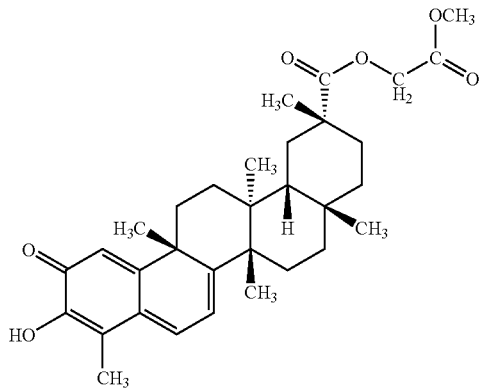
XIII
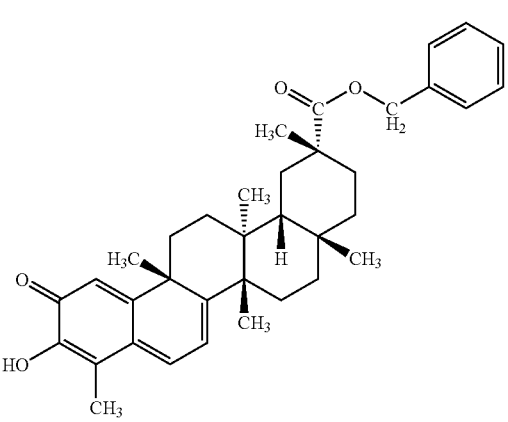
XIV
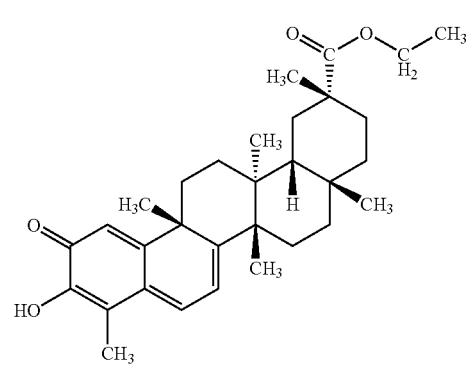
XV
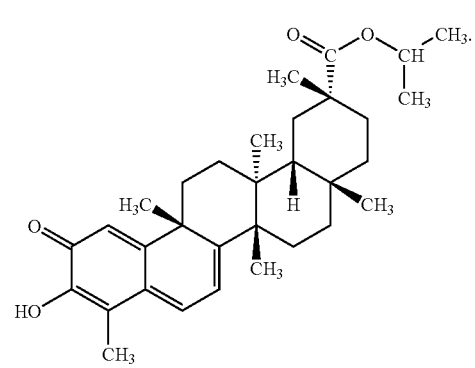
8. The method of claim 7, wherein the celastrol derivative is selected from the group consisting of compounds XIII and XV.

9. A method of treating melanoma in a subject in need thereof comprising administering an effective amount of a celastrol derivative, wherein the celastrol derivative is selected from the group consisting of compounds II, IV-VIII, and XII-XV:

10. The method of claim 9, wherein the administering is via topical administration or subcutaneous administration.

11. The method of claim 9, wherein celastrol derivative is formulated in a pharmaceutical composition.

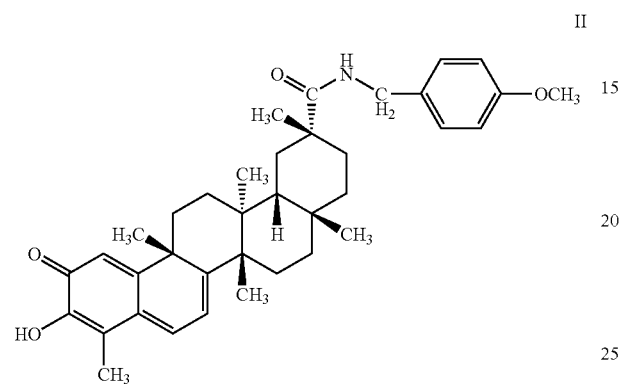

II

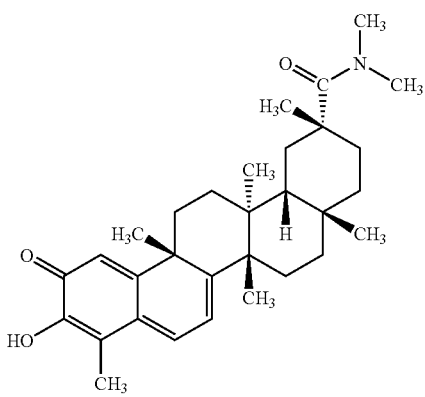

VI

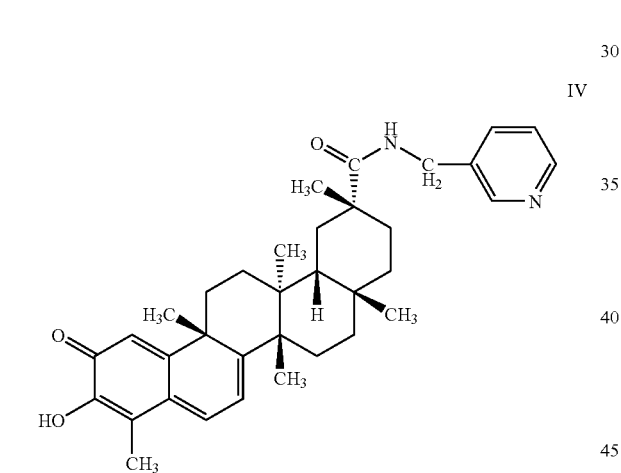

IV

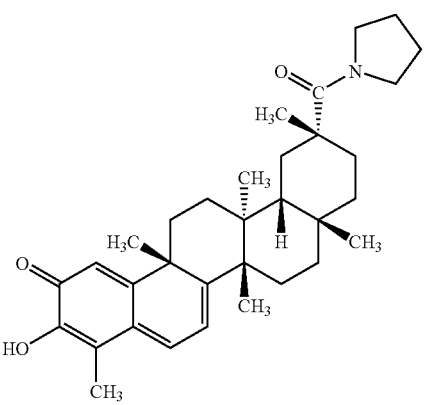

VII

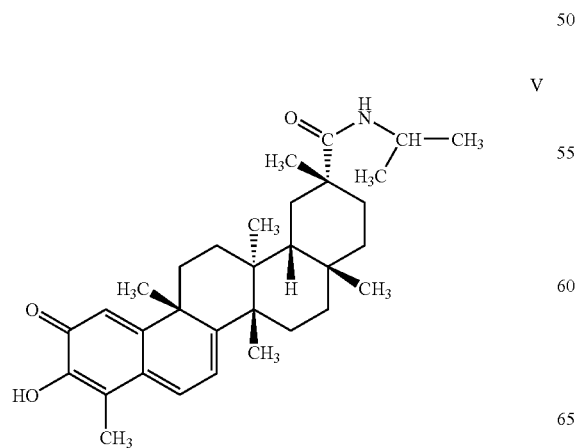

V

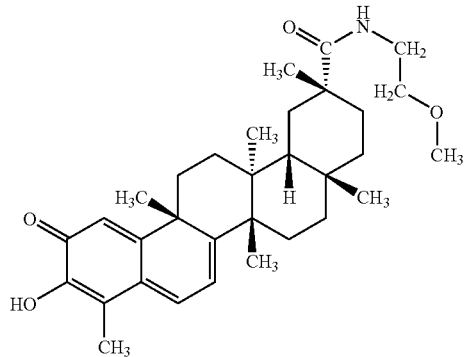

VIII

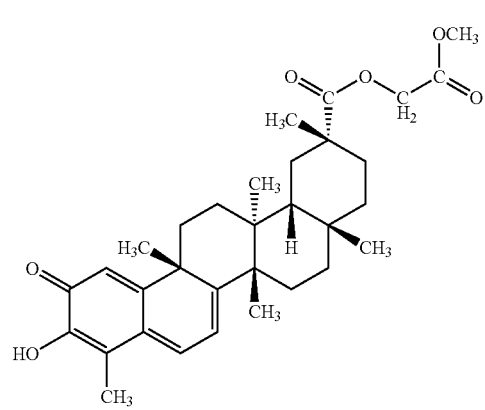
XII
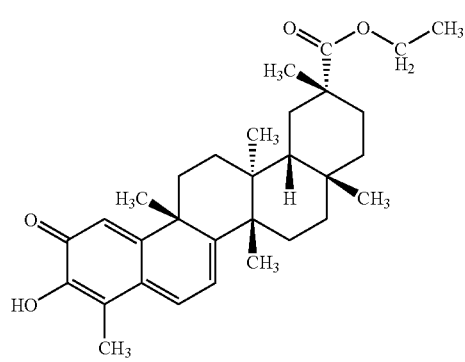
XIV
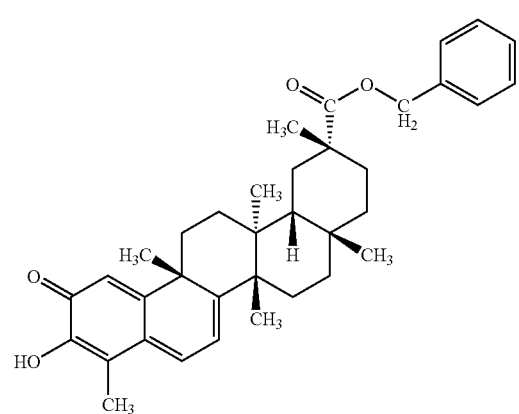
XIII
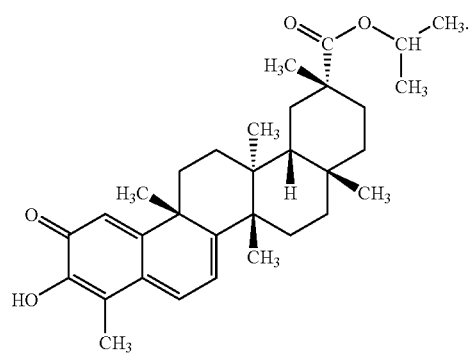
XV
12. The method of claim 9, wherein the celastrol derivative is selected from compounds XIII and XV.
* * * * *